(12) United States Patent
Patel et al.

(10) Patent No.: US 9,458,086 B1
(45) Date of Patent: Oct. 4, 2016

(54) COMPOSITIONS AND METHODS FOR ADIPOCYTE MODULATION

(71) Applicants: Niketa A. Patel, Land O'Lakes, FL (US); Rekha S. Patel, Tampa, FL (US); Kirpal S. Bisht, Tampa, FL (US)

(72) Inventors: Niketa A. Patel, Land O'Lakes, FL (US); Rekha S. Patel, Tampa, FL (US); Kirpal S. Bisht, Tampa, FL (US)

(73) Assignees: University of South Florida (A Florida Non-Profit Corporation), Tampa, FL (US); The United States of America as Represented by the Department of Veterans Affairs Office of General Counsel—PSG IV (024), Washington, DC (US)

( * ) Notice: Subject to any disclaimer, the term of this patent is extended or adjusted under 35 U.S.C. 154(b) by 0 days.

(21) Appl. No.: 14/322,236

(22) Filed: Jul. 2, 2014

Related U.S. Application Data

(60) Provisional application No. 61/842,437, filed on Jul. 3, 2013.

(51) Int. Cl.
   *A61K 31/137* (2006.01)
   *C07C 215/50* (2006.01)
   *A61K 45/06* (2006.01)

(52) U.S. Cl.
   CPC ........... *C07C 215/50* (2013.01); *A61K 31/137* (2013.01); *A61K 45/06* (2013.01)

(58) Field of Classification Search
   USPC ............................ 514/4.8, 6.9, 579, 583, 597
   See application file for complete search history.

(56) References Cited

U.S. PATENT DOCUMENTS

| | | | |
|---|---|---|---|
| 5,674,906 A | 10/1997 | Hatanaka et al. | |
| 7,851,443 B2 | 12/2010 | Bissery et al. | |
| 7,973,076 B2 | 7/2011 | Morinaga et al. | |
| 8,329,743 B2 | 12/2012 | Majeed | |
| 2011/0301159 A1* | 12/2011 | Sayeski ................ | A61K 31/137 514/231.8 |
| 2012/0165281 A1* | 6/2012 | Radominska-Pandya .............. | A61K 31/7034 514/35 |
| 2013/0273175 A1* | 10/2013 | Finley ........................... | 424/635 |

OTHER PUBLICATIONS

Richard; Biochimica et Biophysica Acta, 1842, 2014, 431-439 available online Jun. 2, 2013.*

Jung, et al. "Design, synthesis, and discovery of stilbene derivatives based on lithosperrnic acid B as potent protein tyrosine phosphatase 1B inhibitors", Bioorganic & Medicinal Chemistry Letters, 17:4481-4486, 2007.

Kwon, et al. "Picetannol, natural pholyphenolic stilbene, inhibits adipogenesis via modulation of mitotic clonal expansion and insulin receptor-dependent insulin signaling in early phase of differentiation", J Biol Chem., 287(14):11566-78, 2012.

Apostolatos, et al. "Insulin Promotes Neuronal Survival via the Alternatively Spliced Protein Kinase Cδ11 Isoform", J Biol Bhem., 287(12):9299-9310, 2012.

Sakurai, et al. "Novel Protein Kinase C δ Isoform Insensitive to Caspace-3", Biol. Pharm. Bull., 24(9):973-977, 2001.

Patel, et al. "PKCδ Alternatively Spliced Isoforms Modulate Cellular Apoptosis in Retinoic Acid-Induced Differentiation of Human NT2 Cells and Mouse Embryonic Stem Stells", Gene Expr., 13(2):73-84, 2006.

Jiang, et al. "Identification of a novel antiapoptotic human protein kinase C delta isoform, PKCdeltaVIII in NT2 cells", Biochemistry, 47(2):787-97, 2008.

Wadsworth, et al. "The Utility of Phosphate Carbanions in Olefin Synthesis", J. Am. Chem. Soc., 83:1733-1739, 1961.

Wadsworth, et al. "Synthetic Applications of Phosphoryl-Stabilized Anions", Org. Reactions, 25:73-253, 1977.

Jung, et al. "Synthesis of novel trans-stilbene derivatives and evaluation of their potent antioxidant and neuroprotective effect", Eur. J. Med. Chem., 44(8):3166-3174, 2009.

Saiyed, et al. "Synthesis of stilbene analogues by one-pot oxidation-Wittig and oxidation-Wittig-Heck reaction", Tetrahedron Letters 53(35):4692-4696, 2012.

Ianni, et al. "Reliable and Versatile Synthesis of 2-Aryl-Substituted Cinnamic Acid Esters", Synthesis, 13:2103-2112, 2006.

* cited by examiner

*Primary Examiner* — Pancham Bakshi
(74) *Attorney, Agent, or Firm* — Thomas | Horstemeyer, LLP

(57) ABSTRACT

Modified stilbenoids and formulations thereof are provided. The modified stilbenoids can include one or more amino or amino-alkyl substituents. The formulation can be for the treatment or prevention of obesity and the modified stilbenoid present in an effective amount to alleviate or prevent the onset of one or more symptoms of obesity. Methods of making the modified stilbenoids and formulations thereof are provided. Methods are provided for treating a subject with a modified stilbenoid in an effective amount to alleviate or prevent one or more symptoms associated with diabetes, cardiovascular disease, high blood pressure, deep vein thrombosis, osteoarthritis, obstructive sleep apnea, cancer, and non-alcoholic fatty liver disease. The administration of the modified stilbenoids can result in decreased levels of PKCδII, PKCδVIII, substantially unaltered expression of PKCδI; a decreased number of adipocytes; increased weight and/or fat loss; or a combination thereof.

10 Claims, 14 Drawing Sheets

(a)

| Day | 0 | 0 | 0 | 10 | 10 | 10 |
|---|---|---|---|---|---|---|
| Serum | + | − | − | + | − | − |
| Insulin | − | − | + | − | − | + |

(b)

(a)

(b)

(IIa)

(IIb)

(IIIa)

(IIIb)

(IIIc)

(a)

(b)

(c)

COMPOSITIONS AND METHODS FOR ADIPOCYTE MODULATION

CROSS-REFERENCE TO RELATED APPLICATIONS

This application claims priority to U.S. Ser. No. 61/842,437 filed Jul. 3, 2013.

STATEMENT REGARDING FEDERALLY SPONSORED RESEARCH OR DEVELOPMENT

This invention was made with Government support under grant number ENDA-018-11S awarded by the U.S. Veterans Administration. The U.S. Government has certain rights in the invention.

SEQUENCE LISTING

This application contains a sequence listing filed in electronic form as an ASCII.txt file entitled 292103-1980_ST25.txt, created on Sep. 22, 2014, and having a size of 1740 bytes. The content of the sequence listing is incorporated herein in its entirety.

FIELD OF THE DISCLOSURE

The field of the disclosure is pharmaceutical formulations for treating obesity.

BACKGROUND

American society has become increasingly 'obesogenic' via influences of environments that promote increased food intake and physical inactivity. An excessive amount of body fat or adipose tissue contributes to obesity. Adipose tissue is an important endocrine regulator of energy homeostasis and glucose metabolism. New adipocytes are required for storage of excess energy (intake>expenditure) in white adipose tissue (WAT). Excess adipose tissue mass is the basis of obesity and its associated diseases. Adipose tissue mass is determined by adipocyte size and number. Under circumstances of positive energy balance, there is adipose mass expansion (hypertrophia) and hyperplasia.

The cellular components of adipose tissue also include preadipocytes and stem cells residing in adipose stromal-vascular compartments that differentiate to adipocytes. Given proper environmental and hormonal cues, pre-adipocytes undergo clonal expansion and subsequent terminal differentiation into mature adipocytes. During adipogenesis, expression and activity of PPARγ and C/EBP family and their co-factors promote the morphological and functional changes of a primitive, multipotent state to an adipocyte phenotype characterized by cell shape and lipid accumulations (1-3). 3T3L1 murine preadipocyte cell line (4) is widely used as it authentically reproduces adipogenesis including expression of adipogenic genes and morphological changes. Once these cells are terminally differentiated, they undergo growth arrest and form large spherical intracellular lipid droplets. When these cells are implanted into mice, they are histologically indistinguishable from WAT (5, 6).

Preadipocytes undergo apoptosis while mature adipocytes are not susceptible to apoptosis. This was demonstrated in 3T3L1 preadipocytes which go through apoptosis as shown by DNA fragmentation, Hoescht staining and TUNEL (7, 8). Concomitantly, Bcl2 levels increased as the adipose cells differentiated into mature adipocytes (9-11). This suggested a change in gene expression patterns from preadipocytes to mature adipocytes during adipogenesis. An important mechanism of regulating gene expression during differentiation is alternative splicing which expands the coding capacity of a single gene to produce different proteins with distinct functions (12). Many genes in the apoptosis pathway are alternatively spliced. Divergence observed in gene expression due to alternative splicing may be tissue-specific (13, 14), developmentally regulated (15, 16) or hormonally regulated (17, 18).

Protein Kinase C delta (PKCδ) is a serine/threonine kinase which plays a central role in apoptosis. PKCδ has dual effects: as a mediator of apoptosis and as an anti-apoptosis effecter. Its splice variants, PKCδI and PKCδII, are a switch that determines cell survival and fate. PKCδI promotes apoptosis while PKCδII promotes survival (19). PKCδII is the mouse homolog of human PKCδVIII (20). Both are generated by alternative 5' splice site usage, and their transcripts share >94% sequence homology. It has been shown that PKCδII and PKCδVIII function as pro-survival proteins (21); the functions of the other PKCδ splice variants are not yet established. PKCδII is generated by utilization of an alternative downstream 5' splice site of PKCδ pre-mRNA exon 9. PKCδII, which is resistant to cleavage by caspase-3, arises from insertion of 78 base pairs (bp) (26 amino acids) in its caspase-3 recognition sequence (DILD) (22). Previously, it was also shown that over expression of PKCδII decreased apoptosis and promoted survival in neuronal cells (19).

SUMMARY

Modified stilbenoids are provided. The modified stilbenoids can have a structure according to formula I or a derivative thereof.

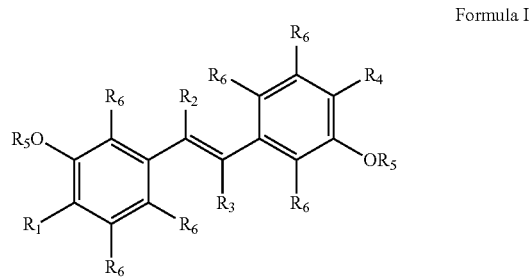

Formula I wherein $R_1$ and $R_4$ are each independently substituted or unsubstituted amino or alkylamino substituents having from 1 to 30 carbon atoms; $R_2$ and $R_3$ are each independently hydrogen or a substituted or unsubstituted alkyl, heteroalkyl, aryl, aralkyl, alkenyl, or alkynyl groups having from 1 to 30 carbon atoms; each $R_5$ is independently hydrogen or a substituted or unsubstituted alkyl, heteroalkyl, aryl, aralkyl, alkenyl, or alkynyl groups having from 1 to 30 carbon atoms; and each $R_6$ is independently hydrogen, halide, hydroxyl, or substituted or unsubstituted alkyl, heteroalkyl, aryl, aralkyl, alkenyl, or alkynyl group having from 1 to 30 carbon atoms. $R_1$ and $R_4$ can each be —$N(R_7)_2$ or —$R_8N(R_7)_2$; wherein each $R_7$ is hydrogen or a substituted or unsubstituted alkyl, heteroalkyl, aryl, aralkyl, alkenyl, or alkynyl group having from 1 to 30 carbon atoms; and $R_8$ is substituted or unsubstituted alkyl or heteroalkyl groups having from 1 to 12 carbon atoms.

The modified stilbenoids can have a structure according to formula II or a derivative thereof.

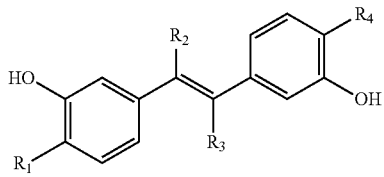

Formula II where $R_1$ and $R_4$ are each independently —$N(R_7)_2$ or —$R_8N(R_7)_2$; each $R_7$ is independently a substituted or unsubstituted alkyl or heteroalkyl group having from 1 to 30 carbon atoms; and $R_8$ is a substituted or unsubstituted alkyl or heteroalkyl group having from 1 to 12 carbon atoms. For example, the modified stilbenoid can have a structure according to Formula III.

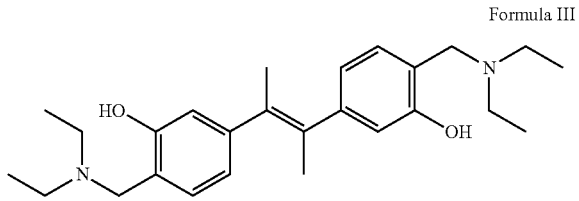 [SMILES: CCN(CC)Cc1ccc(/C(C)=C(\C)c2ccc(CN(CC)CC)c(O)c2)cc1O]

Formula III

Pharmaceutical formulations are provided containing an effective amount of the modified stilbenoids to treat or prevent obesity in a subject in need thereof. The formulations can include one or more additional active agents such as weight-loss or anti-diabetes drugs.

Methods for treating or preventing obesity in a subject in need thereof by administering a therapeutically effective amount of a modified stilbenoid are provided. The modified stilbenoid can contain amino or admino-alkyl substituents, especially the dialkyl-substituted variants thereof. For example, the formulation can contain a therapeutically effective amount of a modified stilbenoid of Formula III. In preferred embodiments the modified stilbenoid is present in an effective amount to alleviate or prevent one or more symptoms associated with diabetes, cardiovascular disease, high blood pressure, deep vein thrombosis, osteoarthritis, obstructive sleep apnea, cancer, and non-alcoholic fatty liver disease. Relative to levels prior to the administration, the subject, after administration of the formulations can demonstrate decreased levels of PKCδII, PKCδVIII, or any homolog thereof; can demonstrate substantially unaltered expression of PKCδI or a homolog thereof; can have a decrease number of adipocites; can have increased weight and/or fat loss; or a combination thereof.

DETAILED DESCRIPTION

Figure 1:
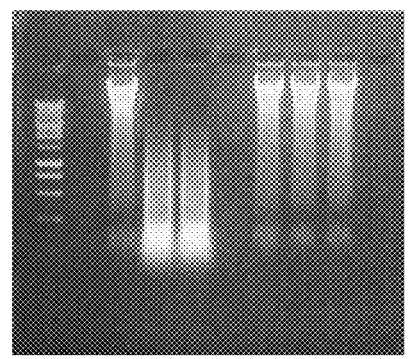
FIG. 1 shows the results of an apoptosis assay: 3T3L1 pre-adipocytes (day 0) underwent apoptosis while mature adipocytes (day 10) did not undergo apoptosis upon serum starvation as seen by (a) DNA fragmentation assay and (b) apoptosis represented as percent Annexin V-PI positive staining using flow cytometry. Experiments were repeated five times. Statistical analysis performed by two-way ANOVA; p>0.75 ns, not significant within group; * p<0.0001 highly significant between day 0 control and serum-deprived; * p<0.0001 highly significant between day 0 and 10 serum deprived.
Figure 1:
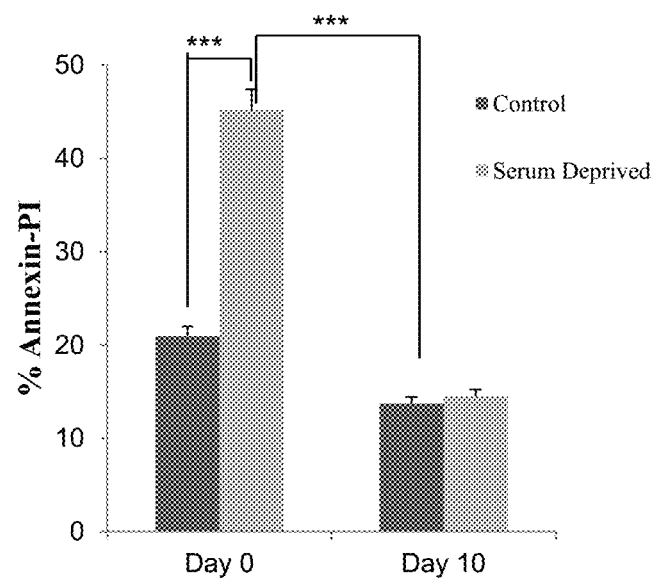

Compositions and methods for increasing weight and/or fat loss in a subject are provided. The compositions can contain modified stilbenoids that specifically inhibit PKCδII expression without substantially inhibiting PKCδI expression. Formulations of these modified stilbenoids can be used for specific modulation of adipocytes, and in some embodiments, specific modulation of adipocyte apoptosis.

I. DEFINITIONS

The term "derivative" refers to any compound having the same or a similar core structure to the compound but having at least one structural difference, including substituting, deleting, and/or adding one or more atoms or functional groups. The term "derivative" does not mean that the derivative is synthesized from the parent compound either as a starting material or intermediate, although this may be the case. The term "derivative" can include salts, prodrugs, or metabolites of the parent compound. Derivatives include compounds in which free amino groups in the parent compound have been derivatized to form amine hydrochlorides, p-toluene sulfoamides, benzoxycarboamides, t-butyloxycarboamides, thiourethane-type derivatives, trifluoroacetylamides, chloroacetylamides, or formamides. Derivatives include compounds in which carboxyl groups in the parent compound have been derivatized to form salts, methyl and ethyl esters or other types of esters or hydrazides. Derivatives include compounds in which hydroxyl groups in the parent compound have been derivatized to form O-acyl or O-alkyl derivatives. Derivatives include compounds in which a hydrogen bond donating group in the parent compound is replaced with another hydrogen bond donating group such as OH, NH, or SH. Derivatives include replacing a hydrogen bond acceptor group in the parent compound with another hydrogen bond acceptor group such as esters, ethers, ketones, carbonates, tertiary amines, imine, thiones, sulfones, tertiary amides, and sulfides.

The terms "biocompatible" and "biologically compatible", as used interchangeably herein, refer to materials that are, with any metabolites or degradation products thereof, generally non-toxic to the recipient, and cause no significant adverse effects to the recipient. Generally speaking, biocompatible materials are materials which do not elicit a significant inflammatory or immune response when administered to a patient. In some embodiments a biocompatible material elicits no detectable change in one or more biomarkers indicative of an immune response. In some embodiments, a biocompatible material elicits no greater than a 10% change, no greater than a 20% change, or no greater than a 40% change in one or more biomarkers indicative of an immune response.

The term "subject" refers to any individual who is the target of administration. The subject can be a vertebrate, for example, a mammal. Thus, the subject can be a human. The term does not denote a particular age or sex. The term "patient" refers to a subject afflicted with a disease or disorder. The term "patient" includes human and veterinary subjects.

The term "treating", as used herein, can include inhibiting the disease, disorder or condition, e.g., impeding its progress; and relieving the disease, disorder, or condition, e.g., causing regression of the disease, disorder and/or condition. Treating the disease, disorder, or condition can include ameliorating at least one symptom of the particular disease, disorder, or condition, even if the underlying pathophysiology is not affected, such as treating the pain of a subject by administration of an analgesic agent even though such agent does not treat the cause of the pain.

The term "preventing", as used herein includes preventing a disease, disorder or condition from occurring in an animal which may be predisposed to the disease, disorder and/or condition but has not yet been diagnosed as having it.

The terms "sufficient" and "effective", as used interchangeably herein, refer to an amount (e.g. mass, volume, dosage, concentration, and/or time period) needed to achieve one or more desired result(s). For example, a therapeutically effective amount refers to an amount needed to achieve one or more therapeutic effects.

The term "pharmaceutically acceptable", as used herein, refers to compounds, materials, compositions, and/or dosage forms which are, within the scope of sound medical judgment, suitable for use in contact with the tissues of human beings and animals without excessive toxicity, irritation, allergic response, or other problems or complications commensurate with a reasonable benefit/risk ratio, in accordance with the guidelines of agencies such as the Food and Drug Administration. A "pharmaceutically acceptable carrier", as used herein, refers to all components of a pharmaceutical formulation which facilitate the delivery of the composition in vivo. Pharmaceutically acceptable carriers include, but are not limited to, diluents, preservatives, binders, lubricants, disintegrators, swelling agents, fillers, stabilizers, and combinations thereof.

"Parenteral administration", as used herein, means administration by any method other than through the digestive tract or non-invasive topical or regional routes. For example, parenteral administration may include administration to a patient intravenously, intradermally, intraperitoneally, intrapleurally, intratracheally, intramuscularly, subcutaneously, subjunctivally, by injection, and by infusion.

"Topical administration", as used herein, means the non-invasive administration to the skin, orifices, or mucosa. Topical administrations can be administered locally, i.e. they are capable of providing a local effect in the region of application without systemic exposure. Topical formulations can provide systemic effect via absorption into the blood stream of the individual. Topical administration can include, but is not limited to, cutaneous and transdermal administration, buccal administration, intranasal administration, intravaginal administration, intravesical administration, ophthalmic administration, and rectal administration.

"Enteral administration", as used herein, means administration via absorption through the gastrointestinal tract. Enteral administration can include oral and sublingual administration, gastric administration, or rectal administration.

"Pulmonary administration", as used herein, means administration into the lungs by inhalation or endotracheal administration. As used herein, the term "inhalation" refers to intake of air to the alveoli. The intake of air can occur through the mouth or nose.

The term "alkyl" refers to the radical of saturated aliphatic groups (i.e., an alkane with one hydrogen atom removed), including straight-chain alkyl groups, branched-chain alkyl groups, cycloalkyl (alicyclic) groups, alkyl-substituted cycloalkyl groups, and cycloalkyl-substituted alkyl groups.

In preferred embodiments, a straight chain or branched chain alkyl has 30 or fewer carbon atoms in its backbone (e.g., $C_1$-$C_{30}$ for straight chains, and $C_3$-$C_{30}$ for branched chains), preferably 20 or fewer, more preferably 15 or fewer, most preferably 10 or fewer. Likewise, preferred cycloalkyls have 3-10 carbon atoms in their ring structure, and more preferably have 5, 6, or 7 carbons in the ring structure. The term "alkyl" (or "lower alkyl") as used throughout the specification, examples, and claims is intended to include both "unsubstituted alkyls" and "substituted alkyls", the latter of which refers to alkyl moieties having one or more substituents replacing a hydrogen on one or more carbons of the hydrocarbon backbone. Such substituents include, but are not limited to, halogen, hydroxyl, carbonyl (such as a carboxyl, alkoxycarbonyl, formyl, or an acyl), thiocarbonyl (such as a thioester, a thioacetate, or a thioformate), alkoxyl, phosphoryl, phosphate, phosphonate, phosphinate, amino, amido, amidine, imine, cyano, nitro, azido, sulfhydryl, alkylthio, sulfate, sulfonate, sulfamoyl, sulfonamido, sulfonyl, heterocyclyl, aralkyl, or an aromatic or heteroaromatic moiety.

Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths. Throughout the application, preferred alkyl groups are lower alkyls. In preferred embodiments, a substituent designated herein as alkyl is a lower alkyl.

It will be understood by those skilled in the art that the moieties substituted on the hydrocarbon chain can themselves be substituted, if appropriate. For instance, the substituents of a substituted alkyl may include halogen, hydroxy, nitro, thiols, amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —$CF_3$, —CN and the like. Cycloalkyls can be substituted in the same manner.

The term "heteroalkyl", as used herein, refers to straight or branched chain, or cyclic carbon-containing radicals, or combinations thereof, containing at least one heteroatom. Suitable heteroatoms include, but are not limited to, O, N, Si, P, Se, B, and S, wherein the phosphorous and sulfur atoms are optionally oxidized, and the nitrogen heteroatom is optionally quaternized. Heteroalkyls can be substituted as defined above for alkyl groups.

The term "alkylthio" refers to an alkyl group, as defined above, having a sulfur radical attached thereto. In preferred embodiments, the "alkylthio" moiety is represented by one of —S-alkyl, —S-alkenyl, and —S-alkynyl. Representative alkylthio groups include methylthio, ethylthio, and the like.

The term "alkylthio" also encompasses cycloalkyl groups, alkene and cycloalkene groups, and alkyne groups. "Arylthio" refers to aryl or heteroaryl groups. Alkylthio groups can be substituted as defined above for alkyl groups.

The terms "alkenyl" and "alkynyl", refer to unsaturated aliphatic groups analogous in length and possible substitution to the alkyls described above, but that contain at least one double or triple bond respectively.

The terms "alkoxyl" or "alkoxy" as used herein refers to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as can be represented by one of —O-alkyl, —O-alkenyl, and —O-alkynyl. The terms "aroxy" and "aryloxy", as used interchangeably herein, can be represented by —O-aryl or O-heteroaryl, wherein aryl and heteroaryl are as defined below. The alkoxy and aroxy groups can be substituted as described above for alkyl.

The terms "amine" and "amino" (and its protonated form) are art-recognized and refer to both unsubstituted and substituted amines, e.g., a moiety that can be represented by the general formula:

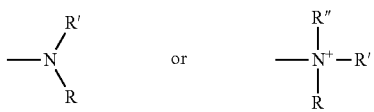

wherein R, R', and R" each independently represent a hydrogen, an alkyl, an alkenyl, —(CH2)$_m$—R$_C$ or R and R' taken together with the N atom to which they are attached complete a heterocycle having from 4 to 8 atoms in the ring structure; R$_C$ represents an aryl, a cycloalkyl, a cycloalkenyl, a heterocycle or a polycycle; and m is zero or an integer in the range of 1 to 8. In preferred embodiments, only one of R or R' can be a carbonyl, e.g., R, R' and the nitrogen together do not form an imide. In still more preferred embodiments, the term "amine" does not encompass amides, e.g., wherein one of R and R' represents a carbonyl. In even more preferred embodiments, R and R' (and optionally R") each independently represent a hydrogen, an alkyl or cycloakly, an alkenyl or cycloalkenyl, or alkynyl. Thus, the term "alkylamine" as used herein means an amine group, as defined above, having a substituted (as described above for alkyl) or unsubstituted alkyl attached thereto, i.e., at least one of R and R' is an alkyl group.

The term "amido" is art-recognized as an amino-substituted carbonyl and includes a moiety that can be represented by the general formula:

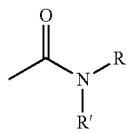

wherein R and R' are as defined above.

"Aryl", as used herein, refers to C$_5$-C$_{10}$-membered aromatic, heterocyclic, fused aromatic, fused heterocyclic, biaromatic, or bihetereocyclic ring systems. Broadly defined, "aryl", as used herein, includes 5-, 6-, 7-, 8-, 9-, and 10-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine, pyrimidine, and the like. Those aryl groups having heteroatoms in the ring structure may also be referred to as "aryl heterocycles" or "heteroaromatics". The aromatic ring can be substituted at one or more ring positions with one or more substituents including, but not limited to, halogen, azide, alkyl, aralkyl, alkenyl, alkynyl, cycloalkyl, hydroxyl, alkoxyl, amino (or quaternized amino), nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —CF$_3$, —CN, and combinations thereof.

The term "aryl" also includes polycyclic ring systems having two or more cyclic rings in which two or more carbons are common to two adjoining rings (i.e., "fused rings") wherein at least one of the rings is aromatic, e.g., the other cyclic ring or rings can be cycloalkyls, cycloalkenyls, cycloalkynyls, aryls and/or heterocycles. Examples of heterocyclic rings include, but are not limited to, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH carbazolyl, carbolinyl, chromanyl, chromenyl, cinnolinyl, decahydroquinolinyl, 2H,6H-1,5,2-dithiazinyl, dihydrofuro[2,3 b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, and xanthenyl. One or more of the rings can be substituted as defined above for "aryl".

The term "aralkyl", as used herein, refers to an alkyl group substituted with an aryl group (e.g., an aromatic or heteroaromatic group).

The term "aralkyloxy" can be represented by —O-aralkyl, wherein aralkyl is as defined above.

The term "carbocycle", as used herein, refers to an aromatic or non-aromatic ring(s) in which each atom of the ring(s) is carbon.

"Heterocycle" or "heterocyclic", as used herein, refers to a monocyclic or bicyclic structure containing 3-10 ring atoms, and preferably from 5-6 ring atoms, consisting of carbon and one to four heteroatoms each selected from the group consisting of non-peroxide oxygen, sulfur, and N(Y) wherein Y is absent or is H, O, (C$_1$-C$_{10}$) alkyl, phenyl or benzyl, and optionally containing 1-3 double bonds and optionally substituted with one or more substituents. Examples of heterocyclic rings include, but are not limited to, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH carbazolyl, carbolinyl, chromanyl, chromenyl, cinnolinyl, decahydroquinolinyl, 2H,6H-1,5,2-dithiazinyl, dihydrofuro[2,3 b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxepanyl, oxetanyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydropyranyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, and xanthenyl. Heterocyclic groups can optionally be substituted with one or more substituents at one or more positions as defined above for alkyl and aryl, for example, halogen, alkyl, aralkyl, alkenyl, alkynyl, cycloalkyl, hydroxyl, amino, nitro, sulfhydryl, imino, amido, phosphate, phosphonate, phosphinate, carbonyl, carboxyl, silyl, ether, alkylthio, sulfonyl, ketone, aldehyde, ester, a heterocyclyl, an aromatic or heteroaromatic moiety, —CF$_3$, —CN, or the like.

The term "carbonyl" is art-recognized and includes such moieties as can be represented by the general formula:

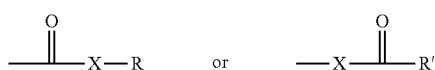

wherein X is a bond or represents an oxygen or a sulfur, and R and R' are as defined above. Where X is an oxygen and R or R' is not hydrogen, the formula represents an "ester". Where X is an oxygen and R is as defined above, the moiety is referred to herein as a carboxyl group, and particularly when R is a hydrogen, the formula represents a "carboxylic acid". Where X is an oxygen and R' is hydrogen, the formula represents a "formate". In general, where the oxygen atom of the above formula is replaced by sulfur, the formula represents a "thiocarbonyl" group. Where X is a sulfur and R or R' is not hydrogen, the formula represents a "thioester." Where X is a sulfur and R is hydrogen, the formula represents a "thiocarboxylic acid." Where X is a sulfur and R' is hydrogen, the formula represents a "thioformate." On the other hand, where X is a bond, and R is not hydrogen, the above formula represents a "ketone" group. Where X is a bond, and R is hydrogen, the above formula represents an "aldehyde" group.

The term "heteroatom" as used herein means an atom of any element other than carbon or hydrogen. Preferred heteroatoms are boron, nitrogen, oxygen, phosphorus, sulfur, and selenium. Other heteroatoms include silicon and arsenic.

As used herein, the term "nitro" means —NO$_2$; the term "halogen" designates —F, —Cl, —Br, or —I; the term "sulfhydryl" means —SH; the term "hydroxyl" means —OH; and the term "sulfonyl" means —SO$_2$—.

The term "substituted" as used herein, refers to all permissible substituents of the compounds described herein. In the broadest sense, the permissible substituents include acyclic and cyclic, branched and unbranched, carbocyclic and heterocyclic, aromatic and nonaromatic substituents of organic compounds. Illustrative substituents include, but are not limited to, halogens, hydroxyl groups, or any other organic groupings containing any number of carbon atoms, preferably 1-14 carbon atoms, and optionally include one or more heteroatoms such as oxygen, sulfur, or nitrogen grouping in linear, branched, or cyclic structural formats. Representative substituents include alkyl, substituted alkyl, alkenyl, substituted alkenyl, alkynyl, substituted alkynyl, phenyl, substituted phenyl, aryl, substituted aryl, heteroaryl, substituted heteroaryl, halo, hydroxyl, alkoxy, substituted alkoxy, phenoxy, substituted phenoxy, aroxy, substituted aroxy, alkylthio, substituted alkylthio, phenylthio, substituted phenylthio, arylthio, substituted arylthio, cyano, isocyano, substituted isocyano, carbonyl, substituted carbonyl, carboxyl, substituted carboxyl, amino, substituted amino, amido, substituted amido, sulfonyl, substituted sulfonyl, sulfonic acid, phosphoryl, substituted phosphoryl, phosphonyl, substituted phosphonyl, polyaryl, substituted polyaryl, $C_3$-$C_{20}$ cyclic, substituted $C_3$-$C_{20}$ cyclic, heterocyclic, substituted heterocyclic, amino acid, peptide, and polypeptide groups.

Heteroatoms such as nitrogen may have hydrogen substituents and/or any permissible substituents of organic compounds described herein which satisfy the valences of the heteroatoms. It is understood that "substitution" or "substituted" includes the implicit proviso that such substitution is in accordance with permitted valence of the substituted atom and the substituent, and that the substitution results in a stable compound, i.e., a compound that does not spontaneously undergo transformation such as by rearrangement, cyclization, elimination, etc.

The term "active derivative" and the like means a derivative herein that retains an ability to specifically inhibit expression of PKCδII, PKCδVIII, or any homolog thereof, in a subject to which it is administered.

The terms "adipocyte", "lipocyte", and "fat cell" are used interchangeably herein to refer to the cells that primarily form adipose tissue and are responsible for things such as energy storage, energy expenditure, lipid homeostasis, and thermogenesis. The ability to store excess energy in adipose tissue is an important evolutionary adaptation, and adipocytes are central to the control of energy balance. There are two main types of fat or adipose tissue: white adipose tissue (WAT), the primary site of energy storage, and brown adipose tissue (BAT), specialized for energy expenditure and thermogenesis. White adipocytes are the most numerous fat cells in the major adipose depots of the body.

The term "thermogenesis" refers to the heat production caused by the metabolic rate activated by exposure to cold. For example, brown adipose cells become activated and exhibit a thermogenic potential in response to proton leak across the mitochondrial membrane. This activation results in heat generation. This functional potential can also be stimulated by exposure to at least one of a catecholamine, like norepinephrine, cyclic AMP and leptin.

The terms "adipose related marker" and "adipogenesis related marker" are used interchangeably herein and include adipocyte markers, brown adipocyte markers and brown adipose-like markers; and white adipocyte markers and white adipose-like markers. Examples of adipocyte markers can include, but are not limited to, lipoprotein lipase (LPL), leptin, glucose transporter-4 (GLUT-4), fatty acid binding protein 4 (aP2), peroxisome proliferator activated receptor α (PPARα) peroxisome proliferator activated receptor γ (PPARγ), adiponectin (AND or ADIPOQ), uncoupling protein 1 (UCP-1), PR domain containing protein 16 (PRDM16), PPAR coactivator-1α (PGC-1α), CCAAT/enhancer binding protein .alpha. (C/EBPα), CCAAT/enhancer binding protein .beta. (C/EBPβ), cell death-inducing DFFA-like effector A (CIDE-A), and elongation of very long chain fatty acids like protein 3 (ELOVL3). Examples of brown adipocyte markers can include, but are not limited to, uncoupling protein 1 (UCP-1), PR domain containing protein 16 (PRDM16), PPAR coactivator-1α (PGC-1α), CCAAT/enhancer binding protein .beta. (C/EBPβ), cell death-inducing DFFA-like effector A (CIDE-A), and elongation of very long chain fatty acids like protein 3 (ELOVL3). White adipocyte markers include homeobox A4 (HoxA4), homeobox C8 (HoxC8), homeobox C9 (HoxC9), leptin, the nuclear corepressor RIP140, and the matrix protein fibrillin-1.

The term "altered level of expression" of a marker, protein or gene refers to an expression level in a test sample (e.g., a sample derived from a subject during or following treatment for a metabolic disorder, such as diabetes and/or obesity), that is greater or less than the standard error of the assay employed to assess expression and may be at least two, three, four, five, six, seven, eight, nine, or ten times the expression level in a control sample (e.g., a sample from the subject prior to treatment), or the average expression level of the marker in several control samples.

The terms "metabolic disorder" includes a disorder, disease or condition caused or characterized at least in part by an abnormal metabolism (i.e., the chemical changes in living cells by which energy is provided for vital processes and activities) in a subject. Metabolic disorders can be associated with aberrant thermogenesis or aberrant adipose cell (e.g., brown or white adipose cell) content or function. Metabolic disorders can be associated with one or more discrete phenotypes. For example, the body mass index (BMI) of a subject is defined as the weight in kilograms divided by the square of the height in meters, such that BMI has units of $kg/m^2$. In some embodiments, "obesity" is defined as the condition wherein the individual has a BMI equal to or greater than 30 $kg/m^2$ (National Institute of Health, Clinical Guidelines on the Identification, Evaluation, and Treatment of Overweight and Obesity in Adults (1998)). However, in some embodiments methods described herein, at least in part, are also intended to include a disease, disorder, or condition that is characterized by a body mass index (BMI) of 25 $kg/m^2$ or more, 26 $kg/m^2$ or more, 27 $kg/m^2$ or more, 28 $kg/m^2$ or more, 29 $kg/m^2$ or more, 29.5 $kg/m^2$ or more, or 29.9 $kg/m^2$ or more, all of which are typically referred to as overweight (National Institute of Health, Clinical Guidelines on the Identification, Evaluation, and Treatment of Overweight and Obesity in Adults (1998)). The obesity may be due to any cause, whether genetic or environmental.

In another aspect, the term obesity is used to mean visceral obesity which can be defined in some embodiments as a waist-to-hip ratio of 1.0 in men and 0.8 in women, which, in another aspect defines the risk for insulin resistance and the development of pre-diabetes. In one embodiment, euglycemia is defined as the condition in which a subject has a fasting blood glucose concentration within the normal range, greater than 70 mg/dl (3.89 mmol/L) and less than 110 mg/dl (6.11 mmol/L). In one embodiment, impaired glucose tolerance (IGT), is defined as the condition in which a subject has a fasting blood glucose concentration or fasting serum glucose concentration greater than 110 mg/dl and less than 126 mg/dl (7.00 mmol/L), or a 2 hour postprandial blood glucose or serum glucose concentration greater than 140 mg/dl (7.78 mmol/L) and less than 200 mg/dl (11.11 mmol/L). The term impaired glucose tolerance is also intended to apply to the condition of impaired fasting glucose. In one embodiment, hyperinsulinemia is defined as the condition in which a subject with insulin resistance, with or without euglycemia, in which the fasting or postprandial serum or plasma insulin concentration is elevated above that of normal, lean individuals without insulin resistance, having a waist-to-hip ratio <1.0 (for men) or <0.8 (for women).

In one embodiment, "prevention of obesity" refers to preventing obesity or an obesity-associated disorder from occurring if the treatment is administered prior to the onset of the obese condition. Moreover, if treatment is commenced in subjects already suffering from or having symptoms of obesity or an obesity-associated disorder, such treatment is expected to prevent, or to prevent the progression of obesity or the obesity-associated disorder.

The term "obesity-associated disorder" includes all disorders associated with or caused at least in part by obesity. Obesity-associated disorders include, for example, diabetes; cardiovascular disease; high blood pressure; deep vein thrombosis; osteoarthritis; obstructive sleep apnea; cancer and non-alcoholic fatty liver disease.

The term "increasing fat loss" includes decreasing the amount of body fat as measured before and after treatment. Body fat percentage can be determined using any method known to one of ordinary skill in the art and includes measurement with calipers or through the use of bioelectrical impedance analysis. Such measurement can be expressed as the subject's body mass index (BMI). In some embodiments, body fat is decreased by decreasing the number of adipocytes and/or increasing adipocyte apoptosis in the subject.

As used herein, "expression" refers to the process by which polynucleotides are transcribed into mRNA and the process by which the transcribed mRNA is subsequently being translated into peptides, polypeptides, or proteins. More particularly, expression includes splicing of the mRNA and an inhibition of expression includes an inhibition of a splicing event. In some embodiments, the modified stilbenoids of the present disclosure inhibit expression of PKCδII, PKCδVIII, or any homolog thereof, by inhibiting the splicing event(s) that results in expression of PKCδII, PKCδVIII, or any homolog thereof.

The term "isolated" means separated from constituents, cellular and otherwise, in which the polynucleotide, peptide, polypeptide, protein, antibody, or fragments thereof, are normally associated with in nature. In one aspect of this disclosure, an isolated polynucleotide is separated from the 3' and 5' contiguous nucleotides with which it is normally associated with in its native or natural environment, e.g., on the chromosome. As is apparent to those of skill in the art, a non-naturally occurring polynucleotide, peptide, polypeptide, protein, antibody, or fragments thereof, does not require "isolation" to distinguish it from its naturally occurring counterpart. In addition, a "concentrated," "separated," or "diluted" polynucleotide, peptide, polypeptide, protein, antibody, or fragments thereof, is distinguishable from its naturally occurring counterpart in that the concentration or number of molecules per volume is greater than "concentrated" or less than "separated" than that of its naturally occurring counterpart. A polynucleotide, peptide, polypeptide, protein, antibody, or fragments thereof, which differs from the naturally occurring counterpart in its primary sequence or for example, by its glycosylation pattern, need not be present in its isolated form since it is distinguishable from its naturally occurring counterpart by its primary sequence, or alternatively, by another characteristic such as glycosylation pattern. Thus, a non-naturally occurring polynucleotide is provided as a separate embodiment from the isolated naturally occurring polynucleotide. A protein produced in a bacterial cell is provided as a separate embodiment from the naturally occurring protein isolated from a eukaryotic cell in which it is produced in nature.

The term "specifically inhibit" is used herein to refer to the action of modified stilbenoids such as SEAM that inhibit expression of PKCδII, PKCδVIII, or any homolog thereof without substantially affecting expression of PKCδI or any homolog thereof.

II. MODIFIED STILBENOIDS AND FORMULATIONS THEREOF

Modified stilbenoids and pharmaceutical formulations thereof are provided. A "modified stilbenoid", as used herein, refers generally to a molecule having a core stilbene structure and one or more substituents or heteroatoms. Modified stilbenoids include stilbene wherein one or more substituents is attached to one or more of the phenyl or ethenyl carbons; wherein one or more of the carbon atoms is replaced by a heteroatom; or a combination thereof. Stilbenoids typically have one or more hydroxy substituents. In preferred embodiments the modifiled stilbenoids have one, two, three, or more hydroxy substituents.

Stilbene and the modified stilbenoinds can have a cis (Z) or a trans (E) configuration with respect to the ethene double bond. Additionally, the substituents in a modified stilbenoid, in some embodiments, can exist in multiple configurations. In some embodiments the modified stilbenoid can be present as a single enantiomer, a purified composition containing essentially one or a few enantiomers, or a racemic mixture containing all or a few possible enantiomers. In preferred embodiments the modified stilbenoid is a trans stilbenoid, i.e. the stilbenoid has a trans configuration with respect to the ethene bond. The modified stilbenoid can be synthetic or semi-synthetic, naturally occurring or non-naturally occurring.

The modified stilbenoid can have a structure according to Formula I or a derivative thereof:

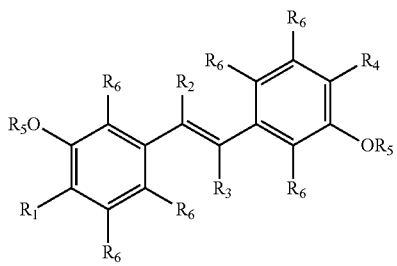

Formula I wherein $R_1$ and $R_4$ are each independently substituted or unsubstituted amino or alkylamino substituents, preferably having from 1 to 30 carbon atoms, from 2 to 20 carbon atoms, or from 3 to 12 carbon atoms; wherein $R_2$ and $R_3$ are each independently hydrogen or substituted or unsubstituted alkyl, heteroalkyl, aryl, aralkyl, alkenyl, or alkynyl groups having from 1 to 30 carbon atoms, from 1 to 20 carbon atoms, or from 1 to 12 carbon atoms; wherein each occurrence of $R_5$ can be independently hydrogen or substituted or unsubstituted alkyl, heteroalkyl, aryl, aralkyl, aralkyl, alkenyl, or alkynyl groups having from 1 to 30 carbon atoms, from 1 to 20 carbon atoms, or from 1 to 12 carbon atoms; and wherein each occurrence of $R_6$ can be independently hydrogen, halide, hydroxyl, or substituted or unsubstituted alkyl, heteroalkyl, aryl, aralkyl, alkenyl, or alkynyl groups having from 1 to 30 carbon atoms, from 1 to 20 carbon atoms, or from 1 to 12 carbon atoms.

$R_1$ and $R_4$ can be independently selected from the group consisting of —$N(R_7)_2$ and —$R_8N(R_7)_2$ wherein each occurrence of $R_7$ can be independently selected from the group consisting of hydrogen, and substituted and unsubstituted alkyl, heteroalkyl, aryl, aralkyl, alkenyl, and alkynyl groups having from 1 to 30 carbon atoms, from 2 to 20 carbon atoms, or from 2 to 12 carbon atoms; and wherein $R_8$ can be a substituted or unsubstituted alkyl or heteroalkyl group having from 1 to 12 carbon atoms, from 1 to 8 carbon atoms, or from 1 to 6 carbon atoms. In preferred embodiments at least one occurrence of $R_7$ is not hydrogen. Suitable $R_7$ and $R_8$ can include methyl, ethyl, or propyl.

The modified stilbenoid can have a structure according to Formula II

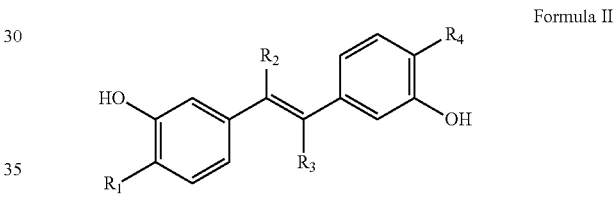

Formula II wherein $R_1$-$R_4$ can be as defined above.

The modified stilbenoid can have a structure according to Formula III

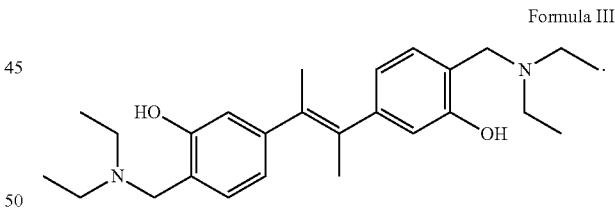

Formula III

The modified stilbenoid according to Formula III is referred to herein as "SEAM".

The modified stilbenoid can include a variety of different substituents as long as the modified stilbenoid is still safe and effective. The modified stilbenoid can include one or more amino or amino-alkyl substituents. The modified stilbenoid can include two or more, preferably two, amino or amino-alkyl substituents. The modified stilbenoid can include one or more dialkyl-amino or dialkyl-amino-alkyl substituents. The modified stilbenoid can include two or more, preferably two, dialkyl-amino or dialkyl-amino-alkyl substituents.

Suitable amino substituents can include —$N(R_7)_2$ wherein each occurrence of $R_7$ can be independently selected from the group consisting of hydrogen, and substituted and unsubstituted alkyl, heteroalkyl, aryl, aralkyl, alkenyl, and alkynyl groups having from 1 to 30 carbon atoms, from 2 to 20 carbon atoms, or from 2 to 12 carbon atoms. Suitable amino-alkyl substituents can include —$R_8N(R_7)_2$ wherein each occurrence of $R_7$ is as defined above and wherein $R_8$ can be a substituted or unsubstituted alkyl or heteroalkyl group having from 1 to 12 carbon atoms, from 1 to 8 carbon atoms, or from 1 to 6 carbon atoms.

Suitable dialkyl-amino substituents can include $N(R_7)_2$ wherein each occurrence of $R_7$ can be independently selected from the group consisting substituted and unsubstituted alkyl, and heteroalkyl groups having from 1 to 30 carbon atoms, from 2 to 20 carbon atoms, or from 2 to 12 carbon atoms. Suitable dialkyl-amino-alkyl substituents can include —$R_8N(R_7)_2$ wherein each occurrence of $R_7$ can be independently selected from the group consisting substituted and unsubstituted alkyl and heteroalkyl groups having from 1 to 30 carbon atoms, from 2 to 20 carbon atoms, or from 2 to 12 carbon atoms, and wherein $R_8$ can be a substituted or unsubstituted alkyl or heteroalkyl group having from 1 to 12 carbon atoms, from 1 to 8 carbon atoms, or from 1 to 6 carbon atoms.

The modified stilbenoid can include one, two, three, four, or more, preferably two, hydroxy or alkoxy substituents. Suitable alkoxy substituents can include —$OR_9$ wherein $R_9$ can be selected from the group consisting substituted and unsubstituted alkyl and heteroalkyl groups having from 1 to 30 carbon atoms, from 2 to 20 carbon atoms, or from 2 to 12 carbon atoms. In some embodiments the modified stilbenoid include two or more, preferably two, hydroxy substituents. The modified stilbenoid can include any combination of the substituents described above.

Pharmaceutical Formulations

Pharmaceutical formulations are provided that contain an effective amount of modified stilbenoid in a pharmaceutical carrier appropriate for administration to an individual in need thereof. The formulations can be administered parenterally (e.g., by injection or infusion), topically (e.g., to the eye), or via pulmonary administration.

Parenteral Formulations

The modified stilbenoid can be formulated for parenteral delivery, such as injection or infusion, in the form of a solution or suspension. The formulation can be administered via any route, such as, the blood stream or directly to the organ or tissue to be treated.

Parenteral formulations can be prepared as aqueous compositions using techniques known in the art. Typically, such compositions can be prepared as injectable formulations, for example, solutions or suspensions; solid forms suitable for using to prepare solutions or suspensions upon the addition of a reconstitution medium prior to injection; emulsions, such as water-in-oil (w/o) emulsions, oil-in-water (o/w) emulsions, and microemulsions thereof, liposomes, or emulsomes.

The carrier can be a solvent or dispersion medium containing, for example, water, ethanol, one or more polyols (e.g., glycerol, propylene glycol, and liquid polyethylene glycol), oils, such as vegetable oils (e.g., peanut oil, corn oil, sesame oil, etc.), and combinations thereof. The proper fluidity can be maintained, for example, by the use of a coating, such as lecithin, by the maintenance of the required particle size in the case of dispersion and/or by the use of surfactants. In many cases, it will be preferable to include isotonic agents, for example, sugars or sodium chloride.

Solutions and dispersions of the modified stilbenoid can be prepared in water or another solvent or dispersing medium suitably mixed with one or more pharmaceutically acceptable excipients including, but not limited to, surfactants, dispersants, emulsifiers, pH modifying agents, and combination thereof.

Suitable surfactants may be anionic, cationic, amphoteric or nonionic surface active agents. Suitable anionic surfactants include, but are not limited to, those containing carboxylate, sulfonate and sulfate ions. Examples of anionic surfactants include sodium, potassium, ammonium of long chain alkyl sulfonates and alkyl aryl sulfonates such as sodium dodecylbenzene sulfonate; dialkyl sodium sulfosuccinates, such as sodium dodecylbenzene sulfonate; dialkyl sodium sulfosuccinates, such as sodium bis-(2-ethylthioxyl)-sulfosuccinate; and alkyl sulfates such as sodium lauryl sulfate. Cationic surfactants include, but are not limited to, quaternary ammonium compounds such as benzalkonium chloride, benzethonium chloride, cetrimonium bromide, stearyl dimethylbenzyl ammonium chloride, polyoxyethylene and coconut amine. Examples of nonionic surfactants include ethylene glycol monostearate, propylene glycol myristate, glyceryl monostearate, glyceryl stearate, polyglyceryl-4-oleate, sorbitan acylate, sucrose acylate, PEG-150 laurate, PEG-400 monolaurate, polyoxyethylene monolaurate, polysorbates, polyoxyethylene octylphenylether, PEG-1000 cetyl ether, polyoxyethylene tridecyl ether, polypropylene glycol butyl ether, Poloxamer® 401, stearoyl monoisopropanolamide, and polyoxyethylene hydrogenated tallow amide. Examples of amphoteric surfactants include sodium N-dodecyl-β-alanine, sodium N-lauryl-β-iminodipropionate, myristoamphoacetate, lauryl betaine and lauryl sulfobetaine.

The formulation can contain a preservative to prevent the growth of microorganisms. Suitable preservatives include, but are not limited to, parabens, chlorobutanol, phenol, sorbic acid, and thimerosal. The formulation may also contain an antioxidant to prevent degradation of the modified stilbenoid.

The formulation is typically buffered to a pH of 3-8 for parenteral administration upon reconstitution. Suitable buffers include, but are not limited to, phosphate buffers, acetate buffers, and citrate buffers.

Water soluble polymers are often used in formulations for parenteral administration. Suitable water-soluble polymers include, but are not limited to, polyvinylpyrrolidone, dextran, carboxymethylcellulose, and polyethylene glycol.

Sterile injectable solutions can be prepared by incorporating the modified stilbenoid in the required amount in the appropriate solvent or dispersion medium with one or more of the excipients listed above, as required, followed by filtered sterilization. Generally, dispersions are prepared by incorporating the various sterilized modified stilbenoids into a sterile vehicle which contains the basic dispersion medium and the required other ingredients from those listed above. In the case of sterile powders for the preparation of sterile injectable solutions, the preferred methods of preparation are vacuum-drying and freeze-drying techniques which yield a powder of the modified stilbenoid plus any additional desired ingredient from a previously sterile-filtered solution thereof. The powders can be prepared in such a manner that the particles are porous in nature, which can increase dissolution of the particles. Methods for making porous particles are well known in the art.

Pharmaceutical formulations for parenteral administration are preferably in the form of a sterile aqueous solution or suspension of particles formed from one or more modified stilbenoids. Acceptable solvents include, for example, water, Ringer's solution, phosphate buffered saline (PBS), and isotonic sodium chloride solution. The formulation may also be a sterile solution, suspension, or emulsion in a nontoxic, parenterally acceptable diluent or solvent such as 1,3-butanediol.

In some instances, the formulation is distributed or packaged in a liquid form. Alternatively, formulations for parenteral administration can be packed as a solid, obtained, for example by lyophilization of a suitable liquid formulation. The solid can be reconstituted with an appropriate carrier or diluent prior to administration.

Solutions, suspensions, or emulsions for parenteral administration may be buffered with an effective amount of buffer necessary to maintain a pH suitable for ocular administration. Suitable buffers are well known by those skilled in the art and some examples of useful buffers are acetate, borate, carbonate, citrate, and phosphate buffers.

Solutions, suspensions, or emulsions for parenteral administration may also contain one or more tonicity agents to adjust the isotonic range of the formulation. Suitable tonicity agents are well known in the art and some examples include glycerin, mannitol, sorbitol, sodium chloride, and other electrolytes.

Solutions, suspensions, or emulsions for parenteral administration may also contain one or more preservatives to prevent bacterial contamination of the ophthalmic preparations. Suitable preservatives are known in the art, and include polyhexamethylenebiguanidine (PHMB), benzalkonium chloride (BAK), stabilized oxychloro complexes (otherwise known as Purite®), phenylmercuric acetate, chlorobutanol, sorbic acid, chlorhexidine, benzyl alcohol, parabens, thimerosal, and mixtures thereof.

Solutions, suspensions, or emulsions for parenteral administration may also contain one or more excipients known art, such as dispersing agents, wetting agents, and suspending agents.

Topical Formulations

The modified stilbenoid can be formulated for topical administration. Suitable dosage forms for topical administration include creams, ointments, salves, sprays, gels, lotions, emulsions, liquids, and transdermal patches. The formulation may be formulated for transmucosal, transepithelial, transendothelial, or transdermal administration. The compositions contain one or more chemical penetration enhancers, membrane permeability agents, membrane transport agents, emollients, surfactants, stabilizers, and combination thereof.

In some embodiments, the conjugates can be administered as a liquid formulation, such as a solution or suspension, a semi-solid formulation, such as a lotion or ointment, or a solid formulation. In some embodiments, the conjugates are formulated as liquids, including solutions and suspensions, such as eye drops or as a semi-solid formulation, such as ointment or lotion for topical application to the skin, to the mucosa, such as the eye or vaginally or rectally.

The formulation may contain one or more excipients, such as emollients, surfactants, emulsifiers, penetration enhancers, and the like.

"Emollients" are an externally applied agent that softens or soothes skin and are generally known in the art and listed in compendia, such as the "Handbook of Pharmaceutical Excipients", 4$^{th}$ Ed., Pharmaceutical Press, 2003. These include, without limitation, almond oil, castor oil, ceratonia extract, cetostearoyl alcohol, cetyl alcohol, cetyl esters wax, cholesterol, cottonseed oil, cyclomethicone, ethylene glycol palmitostearate, glycerin, glycerin monostearate, glyceryl monooleate, isopropyl myristate, isopropyl palmitate, lanolin, lecithin, light mineral oil, medium-chain triglycerides, mineral oil and lanolin alcohols, petrolatum, petrolatum and lanolin alcohols, soybean oil, starch, stearyl alcohol, sunflower oil, xylitol and combinations thereof. In one embodiment, the emollients are ethylhexylstearate and ethylhexyl palmitate.

"Surfactants" are surface-active agents that lower surface tension and thereby increase the emulsifying, foaming, dispersing, spreading and wetting properties of a product. Suitable non-ionic surfactants include emulsifying wax, glyceryl monooleate, polyoxyethylene alkyl ethers, polyoxyethylene castor oil derivatives, polysorbate, sorbitan esters, benzyl alcohol, benzyl benzoate, cyclodextrins, glycerin monostearate, poloxamer, povidone and combinations thereof. In one embodiment, the non-ionic surfactant is stearyl alcohol.

"Emulsifiers" are surface active substances which promote the suspension of one liquid in another and promote the formation of a stable mixture, or emulsion, of oil and water. Common emulsifiers are: metallic soaps, certain animal and vegetable oils, and various polar compounds. Suitable emulsifiers include acacia, anionic emulsifying wax, calcium stearate, carbomers, cetostearyl alcohol, cetyl alcohol, cholesterol, diethanolamine, ethylene glycol palmitostearate, glycerin monostearate, glyceryl monooleate, hydroxypropyl cellulose, hypromellose, lanolin, hydrous, lanolin alcohols, lecithin, medium-chain triglycerides, methylcellulose, mineral oil and lanolin alcohols, monobasic sodium phosphate, monoethanolamine, nonionic emulsifying wax, oleic acid, poloxamer, poloxamers, polyoxyethylene alkyl ethers, polyoxyethylene castor oil derivatives, polyoxyethylene sorbitan fatty acid esters, polyoxyethylene stearates, propylene glycol alginate, self-emulsifying glyceryl monostearate, sodium citrate dehydrate, sodium lauryl sulfate, sorbitan esters, stearic acid, sunflower oil, tragacanth, triethanolamine, xanthan gum and combinations thereof. In one embodiment, the emulsifier is glycerol stearate.

Suitable classes of penetration enhancers are known in the art and include, but are not limited to, fatty alcohols, fatty acid esters, fatty acids, fatty alcohol ethers, amino acids, phospholipids, lecithins, cholate salts, enzymes, amines and amides, complexing agents (liposomes, cyclodextrins, modified celluloses, and diimides), macrocyclics, such as macrocyclic lactones, ketones, and anhydrides and cyclic ureas, surfactants, N-methyl pyrrolidones and derivatives thereof, DMSO and related compounds, ionic compounds, azone and related compounds, and solvents, such as alcohols, ketones, amides, polyols (e.g., glycols). Examples of these classes are known in the art.

An "oil" is a composition containing at least 95% wt of a lipophilic substance. Examples of lipophilic substances include but are not limited to naturally occurring and synthetic oils, fats, fatty acids, lecithins, triglycerides and combinations thereof.

An "emulsion" is a composition containing a mixture of non-miscible components homogenously blended together. In particular embodiments, the non-miscible components include a lipophilic component and an aqueous component. An emulsion is a preparation of one liquid distributed in small globules throughout the body of a second liquid. The dispersed liquid is the discontinuous phase, and the dispersion medium is the continuous phase. When oil is the dispersed liquid and an aqueous solution is the continuous phase, it is known as an oil-in-water emulsion, whereas when water or aqueous solution is the dispersed phase and oil or oleaginous substance is the continuous phase, it is known as a water-in-oil emulsion. Either or both of the oil phase and the aqueous phase may contain one or more surfactants, emulsifiers, emulsion stabilizers, buffers, and other excipients. Preferred excipients include surfactants, especially non-ionic surfactants; emulsifying agents, especially emulsifying waxes; and liquid non-volatile non-aqueous materials, particularly glycols such as propylene glycol. The oil phase may contain other oily pharmaceutically approved excipients. For example, materials such as hydroxylated castor oil or sesame oil may be used in the oil phase as surfactants or emulsifiers.

An emulsion is a preparation of one liquid distributed in small globules throughout the body of a second liquid. The dispersed liquid is the discontinuous phase, and the dispersion medium is the continuous phase. When oil is the dispersed liquid and an aqueous solution is the continuous phase, it is known as an oil-in-water emulsion, whereas when water or aqueous solution is the dispersed phase and oil or oleaginous substance is the continuous phase, it is known as a water-in-oil emulsion. The oil phase can contain a propellant, such as an HFA propellant. Either or both of the oil phase and the aqueous phase may contain one or more surfactants, emulsifiers, emulsion stabilizers, buffers, and other excipients. Preferred excipients include surfactants, especially non-ionic surfactants; emulsifying agents, especially emulsifying waxes; and liquid non-volatile non-aqueous materials, particularly glycols such as propylene glycol. The oil phase may contain other oily pharmaceutically approved excipients. For example, materials such as hydroxylated castor oil or sesame oil may be used in the oil phase as surfactants or emulsifiers.

A "lotion" is a low- to medium-viscosity liquid formulation. A lotion can contain finely powdered substances that are in-soluble in the dispersion medium through the use of suspending agents and dispersing agents. Alternatively, lotions can have as the dispersed phase liquid substances that are immiscible with the vehicle and are usually dispersed by means of emulsifying agents or other suitable stabilizers. In one embodiment, the lotion is in the form of an emulsion having a viscosity of between 100 and 1000 centistokes. The fluidity of lotions permits rapid and uniform application over a wide surface area. Lotions are typically intended to dry on the skin leaving a thin coat of their medicinal components on the skin's surface.

A "cream" is a viscous liquid or semi-solid emulsion of either the "oil-in-water" or "water-in-oil type". Creams may contain emulsifying agents and/or other stabilizing agents. In one embodiment, the formulation is in the form of a cream having a viscosity of greater than 1000 centistokes, typically in the range of 20,000-50,000 centistokes. Creams are often time preferred over ointments as they are generally easier to spread and easier to remove.

The difference between a cream and a lotion is the viscosity, which is dependent on the amount/use of various oils and the percentage of water used to prepare the formulations. Creams are typically thicker than lotions, may have various uses and often one uses more varied oils/butters, depending upon the desired effect upon the skin. In a cream formulation, the water-base percentage is about 60-75% and the oil-base is about 20-30% of the total, with the other percentages being the emulsifier agent, preservatives and additives for a total of 100%.

An "ointment" is a semisolid preparation containing an ointment base and optionally one or more active agents. Examples of suitable ointment bases include hydrocarbon bases (e.g., petrolatum, white petrolatum, yellow ointment, and mineral oil); absorption bases (hydrophilic petrolatum, anhydrous lanolin, lanolin, and cold cream); water-removable bases (e.g., hydrophilic ointment), and water-soluble bases (e.g., polyethylene glycol ointments). Pastes typically differ from ointments in that they contain a larger percentage of solids. Pastes are typically more absorptive and less greasy that ointments prepared with the same components.

A "gel" is a semisolid system containing dispersions of the conjugates in a liquid vehicle that is rendered semisolid by the action of a thickening agent or polymeric material dissolved or suspended in the liquid vehicle. The liquid may include a lipophilic component, an aqueous component or both. Some emulsions may be gels or otherwise include a gel component. Some gels, however, are not emulsions because they do not contain a homogenized blend of immiscible components. Suitable gelling agents include, but are not limited to, modified celluloses, such as hydroxypropyl cellulose and hydroxyethyl cellulose; Carbopol homopolymers and copolymers; and combinations thereof. Suitable solvents in the liquid vehicle include, but are not limited to, diglycol monoethyl ether; alklene glycols, such as propylene glycol; dimethyl isosorbide; alcohols, such as isopropyl alcohol and ethanol. The solvents are typically selected for their ability to dissolve the drug. Other additives, which improve the skin feel and/or emolliency of the formulation, may also be incorporated. Examples of such additives include, but are not limited, isopropyl myristate, ethyl acetate, $C_{12}$-$C_{15}$ alkyl benzoates, mineral oil, squalane, cyclomethicone, capric/caprylic triglycerides, and combinations thereof.

Foams can include an emulsion in combination with a gaseous propellant. The gaseous propellant can include hydrofluoroalkanes (HFAs). Suitable propellants include HFAs such as 1,1,1,2-tetrafluoroethane (HFA 134a) and 1,1,1,2,3,3,3-heptafluoropropane (HFA 227), but mixtures and admixtures of these and other HFAs that are currently approved or may become approved for medical use are suitable. The propellants preferably are not hydrocarbon propellant gases which can produce flammable or explosive vapors during spraying. Furthermore, the compositions preferably contain no volatile alcohols, which can produce flammable or explosive vapors during use.

Buffers are used to control pH of a composition. Preferably, the buffers buffer the composition from a pH of about 4 to a pH of about 7.5, more preferably from a pH of about 4 to a pH of about 7, and most preferably from a pH of about 5 to a pH of about 7. In a preferred embodiment, the buffer is triethanolamine.

Preservatives can be used to prevent the growth of fungi and microorganisms. Suitable antifungal and antimicrobial agents include, but are not limited to, benzoic acid, butylparaben, ethyl paraben, methyl paraben, propylparaben, sodium benzoate, sodium propionate, benzalkonium chloride, benzethonium chloride, benzyl alcohol, cetylpyridinium chloride, chlorobutanol, phenol, phenylethyl alcohol, and thimerosal.

In certain embodiments, it may be desirable to provide continuous delivery of one or more conjugates to a patient in need thereof. For topical applications, repeated application can be done or a patch can be used to provide continuous administration of the noscapine analogs over an extended period of time.

Enteral Formulations

The conjugates can be prepared in enteral formulations, such as for oral administration. Suitable oral dosage forms include tablets, capsules, solutions, suspensions, syrups, and lozenges. Tablets can be made using compression or molding techniques well known in the art. Gelatin or non-gelatin capsules can prepared as hard or soft capsule shells, which can encapsulate liquid, solid, and semi-solid fill materials, using techniques well known in the art.

Formulations are prepared using pharmaceutically acceptable carriers. As generally used herein "carrier" includes, but is not limited to, diluents, preservatives, binders, lubricants, disintegrators, swelling agents, fillers, stabilizers, and combinations thereof. Polymers used in the dosage form include hydrophobic or hydrophilic polymers and pH dependent or independent polymers. Preferred hydrophobic and hydrophilic polymers include, but are not limited to, hydroxypropyl methylcellulose, hydroxypropyl cellulose, hydroxyethyl cellulose, carboxy methylcellulose, polyethylene glycol, ethylcellulose, microcrystalline cellulose, polyvinyl pyrrolidone, polyvinyl alcohol, polyvinyl acetate, and ion exchange resins.

Carrier also includes all components of the coating composition which may include plasticizers, pigments, colorants, stabilizing agents, and glidants.

Formulations can be prepared using one or more pharmaceutically acceptable excipients, including diluents, preservatives, binders, lubricants, disintegrators, swelling agents, fillers, stabilizers, and combinations thereof.

Delayed release dosage formulations can be prepared as described in standard references such as "Pharmaceutical dosage form tablets", eds. Liberman et. al. (New York, Marcel Dekker, Inc., 1989), "Remington—The science and practice of pharmacy", 20th ed., Lippincott Williams & Wilkins, Baltimore, Md., 2000, and "Pharmaceutical dosage forms and drug delivery systems", 6th Edition, Ansel et al., (Media, Pa.: Williams and Wilkins, 1995). These references provide information on excipients, materials, equipment and process for preparing tablets and capsules and delayed release dosage forms of tablets, capsules, and granules. These references provide information on carriers, materials, equipment and process for preparing tablets and capsules and delayed release dosage forms of tablets, capsules, and granules.

The conjugates may be coated, for example to delay release once the particles have passed through the acidic environment of the stomach. Examples of suitable coating materials include, but are not limited to, cellulose polymers such as cellulose acetate phthalate, hydroxypropyl cellulose, hydroxypropyl methylcellulose, hydroxypropyl methylcellulose phthalate and hydroxypropyl methylcellulose acetate succinate; polyvinyl acetate phthalate, acrylic acid polymers and copolymers, and methacrylic resins that are commercially available under the trade name EUDRAGIT® (Roth Pharma, Westerstadt, Germany), zein, shellac, and polysaccharides.

Coatings may be formed with a different ratio of water soluble polymer, water insoluble polymers and/or pH dependent polymers, with or without water insoluble/water soluble non polymeric excipient, to produce the desired release profile. The coating is either performed on dosage form (matrix or simple) which includes, but not limited to, tablets (compressed with or without coated beads), capsules (with or without coated beads), beads, particle compositions, "ingredient as is" formulated as, but not limited to, suspension form or as a sprinkle dosage form.

Examples of suitable coating materials include, but are not limited to, cellulose polymers such as cellulose acetate phthalate, hydroxypropyl cellulose, hydroxypropyl methylcellulose, hydroxypropyl methylcellulose phthalate and hydroxypropyl methylcellulose acetate succinate; polyvinyl acetate phthalate, acrylic acid polymers and copolymers, and methacrylic resins that are commercially available under the trade name EUDRAGIT® (Roth Pharma, Westerstadt, Germany), zein, shellac, and polysaccharides.

Additionally, the coating material may contain conventional carriers such as plasticizers, pigments, colorants, glidants, stabilization agents, pore formers and surfactants.

Optional pharmaceutically acceptable excipients include, but are not limited to, diluents, binders, lubricants, disintegrants, colorants, stabilizers, and surfactants. Diluents, also referred to as "fillers," are typically necessary to increase the bulk of a solid dosage form so that a practical size is provided for compression of tablets or formation of beads and granules. Suitable diluents include, but are not limited to, dicalcium phosphate dihydrate, calcium sulfate, lactose, sucrose, mannitol, sorbitol, cellulose, microcrystalline cellulose, kaolin, sodium chloride, dry starch, hydrolyzed starches, pregelatinized starch, silicone dioxide, titanium oxide, magnesium aluminum silicate and powdered sugar.

Binders are used to impart cohesive qualities to a solid dosage formulation, and thus ensure that a tablet or bead or granule remains intact after the formation of the dosage forms. Suitable binder materials include, but are not limited to, starch, pregelatinized starch, gelatin, sugars (including sucrose, glucose, dextrose, lactose and sorbitol), polyethylene glycol, waxes, natural and synthetic gums such as acacia, tragacanth, sodium alginate, cellulose, including hydroxypropylmethylcellulose, hydroxypropylcellulose, ethylcellulose, and veegum, and synthetic polymers such as acrylic acid and methacrylic acid copolymers, methacrylic acid copolymers, methyl methacrylate copolymers, aminoalkyl methacrylate copolymers, polyacrylic acid/polymethacrylic acid and polyvinylpyrrolidone.

Lubricants are used to facilitate tablet manufacture. Examples of suitable lubricants include, but are not limited to, magnesium stearate, calcium stearate, stearic acid, glycerol behenate, polyethylene glycol, talc, and mineral oil.

Disintegrants are used to facilitate dosage form disintegration or "breakup" after administration, and generally include, but are not limited to, starch, sodium starch glycolate, sodium carboxymethyl starch, sodium carboxymethylcellulose, hydroxypropyl cellulose, pregelatinized starch, clays, cellulose, alginine, gums or cross linked polymers, such as cross-linked PVP (Polyplasdone® XL from GAF Chemical Corp).

Stabilizers are used to inhibit or retard drug decomposition reactions which include, by way of example, oxidative reactions. Suitable stabilizers include, but are not limited to, antioxidants, butylated hydroxytoluene (BHT); ascorbic acid, its salts and esters; Vitamin E, tocopherol and its salts; sulfites such as sodium metabisulphite; cysteine and its derivatives; citric acid; propyl gallate, and butylated hydroxyanisole (BHA).

Diluents, also referred to as "fillers," are typically necessary to increase the bulk of a solid dosage form so that a practical size is provided for compression of tablets or formation of beads and granules. Suitable diluents include, but are not limited to, dicalcium phosphate dihydrate, calcium sulfate, lactose, sucrose, mannitol, sorbitol, cellulose, microcrystalline cellulose, kaolin, sodium chloride, dry starch, hydrolyzed starches, pregelatinized starch, silicone dioxide, titanium oxide, magnesium aluminum silicate and powdered sugar. The usual diluents include inert powdered substances such as starches, powdered cellulose, especially crystalline and microcrystalline cellulose, sugars such as fructose, mannitol and sucrose, grain flours and similar edible powders. Typical diluents include, for example, various types of starch, lactose, mannitol, kaolin, calcium phosphate or sulfate, inorganic salts such as sodium chloride and powdered sugar. Powdered cellulose derivatives are also useful. Typical tablet binders include substances such as starch, gelatin and sugars such as lactose, fructose, and glucose. Natural and synthetic gums, including acacia, alginates, methylcellulose, and polyvinylpyrrolidone can also be used. Polyethylene glycol, hydrophilic polymers, ethylcellulose and waxes can also serve as binders. A lubricant is necessary in a tablet formulation to prevent the tablet and punches from sticking in the die. The lubricant is chosen from such slippery solids as talc, magnesium and calcium stearate, stearic acid and hydrogenated vegetable oils.

The preferred coating weights for particular coating materials may be readily determined by those skilled in the art by evaluating individual release profiles for tablets, beads and granules prepared with different quantities of various coating materials. It is the combination of materials, method and form of application that produce the desired release characteristics, which one can determine only from the clinical studies.

Additional Active Agents

The modified stilbenoid formulations can contain one or more additional active agents including, but not limited to, weight-loss drugs and anti-diabetes drugs.

A "weight-loss drug", as used herein, includes a drug that increases adipocyte apoptosis, enhances BAT expansion, increases thermogenic activity in BAT, increases beige/brite adipocyte differentiation in WAT, or enhances WAT browning. Norepinephrine increases thermogenesis in BAT. Thermogenesis is also affected by UCP1, a brown adipocyte-specific molecular marker. Hormones, cytokines, and other circulating factors can help control BAT activity. Thiazolidinedione, has been shown to increase the metabolic activity of BAT and to be involved in the browning of WAT. Prostaglandins enhance WAT browning. Weight-loss drugs can be lipase inhibitors, appetite suppressants, thyroid drugs, laxatives, diuretics.

III. METHODS OF MAKING MODIFIED STILBENOIDS

The modified stilbenoids can be synthesized by any method known to those skilled in the art of synthetic chemistry. Modified stilbenoids can be prepared, for example by aldol condensation, by a Wittig or Wittig-Horner reaction, by Heck coupling, by Negeshi-Stille reaction, by McMurry coupling, or by a Perkin reaction.

Aldol-type condensation of an aromatic aldehyde with activated methylarene or phenylacetic acid is a useful reaction for preparing stilbene derivatives. By starting with a substituted toluene and/or a substituted aromatic aldehyde, aldo-type condensation can be used to produce substituted stilbenes. For example, starting from para-substituted toluenes or para-substituted aromatic aldehydes, one can obtain 4,4'-disubstituted stilbenene. The general reaction for an aldol condensation can look like:

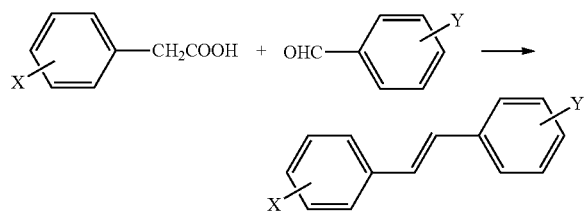

where the aldehyde is activated, for example, by the extraction of a proton using an acid such as NaOH or piperidine.

The Wittig reaction is the reaction of an aldehyde or ketone with a triphenyl phosphonium glide to give an alkene and triphenylphosphine oxide. A variety of substituted stilbenes have been prepared by Witting reaction (see for example, Wadsworth et al., *J. Am. Chem. Soc.,* 1961, 83:1733-1739; Wadsworth, Org. Reactions, 1977, 25:73-253; Kelly, *Comp. Org. Synth.,* 1991, 1:729-817; and Ianni et al., *Synthesis,* 2006, 2103-2112). Numerous variations of the Wittig reaction have been developed for the synthesis of symmetrical and unsymmetrical stilbene derivatives (Jung et al., *Eur. J. Med. Chem.,* 2009, 44(8):3166-3174; Saiyed et al., *Tetrahedron Lett.* 2012, 53(35):4692-4696).

McMurry coupling is a reductive coupling reaction in which two ketone or aldehyde groups are coupled to an alkene in the presence of a catalyst such as titanium (III) chloride and a reducing agent. A combination of alkali metal salts, particularly potassium chloride, with low-valent titanium reagents generated from titanium chlorides with lithium or magnesium in either THF or DME are effective reagents for stereoselective McMurry coupling reactions of aldehydes and ketones to substituted alkenes. In some embodiments a stilbenoid is amino alkylated by Mannich reaction.

IV. METHODS OF USING MODIFIED STILBENOIDS AND FORMULATIONS THEREOF

The modified stilbenoids and pharmaceutical formulations thereof can be used to treat diseases and disorders including metabolic diseases and disorders and obesity. Metabolic diseases include obesity, hyperlipidemia and insulin resistance or a disease associated with a lack of mitochondria, e.g., diabetes, neurodegeneration, and aging. In some embodiments the metabolic disorder is obesity, insulin resistance, hyperinsulinemia, hypoinsulinemia, type II diabetes, hypertension, hyperhepatosteatosis, hyperuricemia, fatty liver, non-alcoholic fatty liver disease, polycystic ovarian syndrome, acanthosis nigricans, hyperphagia, endocrine abnormalities, triglyceride storage disease, Bardet-Biedl syndrome, Lawrence-Moon syndrome, Prader-Labhart-Willi syndrome, or muscle hypoplasia. Treatment of the obesity facilitates treatment of obesity-associated disorders such as diabetes; cardiovascular disease; high blood pressure; deep vein thrombosis; osteoarthritis; obstructive sleep apnea; cancer and non-alcoholic fatty liver disease.

The methods and compositions are useful for the treatment of diseases, including metabolic diseases and weight-related disorders. To treat obesity, the methods include inducing WAT in a subject to change into BAT or brown-like adipose tissue; inducing differentiation of WAT into brown adipose-like cells; inducing differentiation of stem/progenitor cells to brown adipose cells; increasing adipocyte apoptosis or decreasing adipogenesis, especially for WAT adipocytes; or a combination thereof.

In some embodiments, the methods include identifying a subject in need of treatment (e.g., an overweight or obese subject, e.g., with a body mass index (BMI) of 25-29 or 30 or above or a subject with a weight related disorder) and administering to the subject an effective amount of the modified stilbenoid. A subject in need of treatment can be selected based on the subject's body weight or body mass index. In some embodiments, the methods include evaluating the subject for one or more of: weight, adipose tissue stores, adipose tissue morphology, insulin levels, insulin metabolism, glucose levels, thermogenic capacity, and cold sensitivity. Adipocyte differentiation may be detected through expression of one or more adipose related markers.

Dosage regimens may be adjusted to provide the optimum desired response (e.g., a therapeutic or prophylactic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier.

In the preferred embodiments, the modified stilbenoied are administered by injection intravenously, intramuscularly, intraperitoneally, or subcutaneously.

It should also be understood that the foregoing relates to preferred embodiments of the present disclosure and that numerous changes may be made therein without departing from the scope of the disclosure. The disclosure is further illustrated by the following examples, which are not to be construed in any way as imposing limitations upon the scope thereof. On the contrary, it is to be clearly understood that resort may be had to various other embodiments, modifications, and equivalents thereof, which, after reading the description herein, may suggest themselves to those skilled in the art without departing from the spirit of the present disclosure and/or the scope of the appended claims. All patents, patent applications, and publications referenced herein are incorporated by reference in their entirety for all purposes.

EXAMPLES

Example 1

The following materials and methods were used in the subsequent Examples.

Cell Culture:

Mouse 3T3-L1 preadipocytes were purchased from Zen-Bio™ (Research Triangle Park, N.C., USA) and passaged as preconfluent cultures in DMEM high glucose (Invitrogen, Carlsbad, Calif.) with 10% newborn calf serum (Sigma-Aldrich, St. Louis, Mo.) at 37° C. and 10% $CO_2$. Once confluent, cells were differentiated (day 0) in DMEM high glucose with 10% fetal bovine serum (Atlas Biological, Fort Collins, Colo.), 10 μg/mL bovine insulin (Sigma), 1 mM dexamethasone (Sigma), and 0.5 mM isobutyl-1-methylxanthine (Sigma). On day 2, media was replaced with DMEM high glucose, 10% FBS, and bovine insulin. Day 4 and afterwards, cells were cultured in DMEM high glucose plus 10% FBS.

Animal Studies:

Total RNA was obtained from mouse adipose tissues from Dr. You (University of South Florida). 8-week old male C57BL/6J (Jackson labs) were either fed a chow diet (control) or diet with added 400 mg resveratrol per kg body weight, once daily 23); n=5. Total RNA was extracted from adipose tissues from these mice. All protocols were reviewed and approved by the Institutional Animal Care and Use Committee at University of South Florida, Division of Comparative Medicine.

Western Blot Analysis:

Protein lysates were obtained from 3T3L1 cells using lysis buffer containing proteases. Protein lysates (40 μg) were separated by SDS-PAGE with 10% gels. Proteins were electrophoretically transferred to nitrocellulose membranes, blocked with Tris-buffered saline containing 0.1% Tween 20 and 5% nonfat dried milk, washed, and incubated with a polyclonal anti-PARP (Upstate Biotechnology), anti-XIAP (AnaSpec), anti-Bcl2, anti-caspase 9 (Calbiochem), anti-Bcl-x (Santa Cruz Biotechnology), and anti-PKCδ (Cell Signaling) or antibody against the hinge-region of PKCδII (Patel lab (19)). This antibody is specific for PKCδII, as it recognizes the extended hinge region, which is absent in PKCδI (24). Other antibodies used are as follows: PPARγ, Akt, pAkt 473, TNFα, Adiponectin, p-BAD (S316), p-PTEN (Cell Signaling, Boston, Mass.), β-actin A5441 (Sigma). After incubation with anti-rabbit IgG-HRP, enhanced chemiluminescence (Pierce) was used for detection. FluorChem M™ (Protein Simple) imaging system was used to capture digital chemiluminescence images and process western blots. Data was analyzed using AlphaView® software.

Co-Immunoprecipitation:

Co-immunoprecipitation was performed with BAD antibody (Cell Signaling) using Protein A Magnetic Beads #S1425S (New England Biolabs, NEB, Ipswich, Mass.) according to the manufacturer's protocol. The samples were then analyzed as described above in western blot analysis.

RT-PCR:

Total RNA was isolated from 3T3L1 cells with RNA-Bee (Tel Test Center) as recommended by the manufacturer. RNA was also obtained from adipose tissues of mice fed with or without resveratrol. 2 μg RNA was used to synthesize first-strand cDNA with an Oligo(dT) primer and Omniscript R kit (Qiagen). The following primers were used in PCR: PKCδ forward primer 5' GTGGCCAACCTGTGTG-GTATCAAC 3' (SEQ ID NO:1); reverse primer 5' CTCT-GCCAGCAGCACCTTGCCAA 3' (SEQ ID NO:2). These primers amplified PKCδI and PKCδII simultaneously. PKCδII-specific antisense primer (5' TCGCAGGTCTAC-TACTGTCCTTTTCC3') (SEQ ID NO:3). β-actin forward primer 5' CTTCATTGACCTCAACTCATG 3' (SEQ ID NO:4); reverse primer 5' TGTCATGGATGACCTTGGC-CAG 3' (SEQ ID NO:5). Following PCR, 5% of products were resolved on 6% PAGE gels and detected by silver staining. The PCR reaction was optimized for linear range amplification to allow for quantification of products. Densitometric analyses of the bands were done using the Un-Scan IT™ Analysis Software (Silk Scientific).

siRNA Transfection:

Custom siRNA for PKCδII (19) and scrambled siRNA were purchased from Ambion. These siRNA were previously validated for specificity and off-target gene effects were eliminated. The siRNAs were transfected for 48-72 hours using siPORT NeoFX® transfection agent or electroporated using Nucleofector® (Lonza).

DNA Laddering Protocol:

DNA laddering was used to identify DNA cleavage that occurs during apoptosis. Pellets containing $1 \times 10^6$ cells from the attached and floating cell population were washed in PBS and resuspended in 20 μl of Solution I (10 mM EDTA, 50 mM Tris-HCl (pH 8.0), 0.5% (w/v) SDS) plus proteinase K (20 mg/ml stock, used at 0.5 mg/ml). Samples were incubated at 50° C. for 1 hour, 10 μl of 0.5 mg/ml RNaseA was added, and the samples were incubated at 50° C. for 1 hour. The samples were heated rapidly to 70° C., supplemented with 10 μl of Solution II (10 mM EDTA, 1% (w/v)

low-melting-point agarose, 40% (w/v) sucrose, 0.25% (w/v) bromophenol blue), and immediately loaded onto a 2% agarose gel containing 0.1 μg/ml ethidium bromide (stock=10 mg/ml). The gel was cooled to 4° C. for approximately 5 minutes to allow the samples to set in the wells, and then run in Tris-acetate buffer at 40 V until the dye front migrates 4-5 cm. The DNA was observed by UV transillumination and photographed.

Cytotoxicity Assay:

WST-1 (Roche Molecular Biochemicals, IN) was added to 3T3L1 cells (in triplicate) that are treated without or with SEAM to a final concentration of 10% (vol/vol). Cells were incubated for 2 hours at 37° C. The formazon dye produced by viable cells was quantified using a spectrophotometer set at a wavelength of 440 nm and absorbance recorded for each well (reference wavelength, 690 nm).

Transient Transfection of Plasmid DNA:

3T3L1 pre-adipocytes were trypsinized and cell pellets were collected in 100 μL Nucleofector® solution (Lonza) and combined with plasmid DNA (2 μg). The cell/DNA solution was transferred to a cuvette and the program started (0.34 kV, 960 microfarads). 500 μL of medium was added immediately and cells were gently transferred to 60 mm plates and allowed to differentiate.

Apoptosis Assay:

3T3L1 preadipocytes were cultured on 60 mm dishes as described above. For apoptosis assays, cells were serum-starved for 48 hours. Media were collected and cells were washed one time with HBSS and then trypsinized for 5.0 minutes. Five ml complete media was added to neutralize the trypsin. Media and washes were pooled and centrifuged at 1200 RPMS for five minutes. Cells were washed one time with PBS and one time with binding buffer and then incubated for 15 minutes with 5.0 μl AV-FITC and 5.0 μl PI in 100 μl binding buffer (BD Pharmagen, San Diego, Calif.) at room temperature in the dark. 400 μl binding buffer was added and cells were analyzed by flow cytometry within one hour Annexin V-FITC and PI fluorescence, which stains apoptotic cells, were measured using an Accuri C6 flow cytometer.

Oil Red O Staining:

3T3L1 preadipocytes were washed with PBS and fixed with 10% formalin for 30 minutes. The cells were then rinsed and incubated with 60% isopropanol for 5 minutes. Oil Red O stain (0.15%, Sigma) was added and incubated for 10 minutes. Images were captured with Nixon confocal microscope.

Synthesis of SEAM:

SEAM (synthesized in Bisht Lab, Department of Chemistry, University of South Florida) was envisioned using Mcmurry coupling of the 3-hydroxyacetophenone to synthesize the corresponding 3-hydroxystilbene followed by the Mannich coupling with the diethylamine and formaldehyde.

Synthesis of 3,3'-[1,2-dimethyl-1,2-ethenediyl]bis phenol

In a flame dried 2 neck round bottom flask fitted with magnetic stirrer bar and reflux condensor, dry THF (180 mL or 1.5 Molar) and Zinc (8 equivalents) were taken under $N_2$ atmosphere. Then the reaction mixture was cooled to 0° C. in an ice bath. To this mixture TiCl4 (4 equivalents) was added dropwise while maintaining the reaction temperature at 0° C. After addition was complete, reaction mixture was refluxed for 2 hours and cooled to 0° C. 3-Hydroxyacetophenone (1 equivalent) solution in dry THF was added to the reaction mixture slowly. The reaction mixture was then allowed to reflux until TLC (2:3 mixture of ethylacetate/hexane) showed that all the 3-Hydroxyacetophenone was consumed. Upon completion, the reaction mixture was concentrated, diluted with ethylacetate and treated with saturated $K_2CO_3$ solution under stirring for 7 hours. The reaction mixture was filtered and extracted with ethylacetate. The stilbene (3,3'-[1,2-dimethyl-1,2-ethenediyl]bis Phenol) was purified upon silica gel chromatographic separation (76% yield). 1H NMR (250 MHz, d6-DMSO): 9.1 (bs, 2H), 7.1 (m, J=7.75 Hz), 6.88 (t, 2H, J=7.75 Hz), 6.6 (m), 6.4 (m, 6H), 2.0 (s, 6H), 1.8 (s); 13C NMR (62.5 MHz, d6-DMSO): 157.1, 156.5, 145.6, 131.9, 129.1, 128.4, 119.6, 115.5, 112.6, 22.0, 21.4.

Synthesis of SEAM (3,3'-(1,2-Dimethyl-1,2-ethenediyl)bis[2-[(diethylamino)methyl]phenol)

To a solution of 3,3'-[1,2-Dimethyl-1,2-ethenediyl]bis phenol (1 equivalent) in 15 mL of methanol was added paraformaldehyde (2.1 equivalents) and amine (2.2 equivalents). The reaction mixture was refluxed until completion. The mixture was cooled, concentrated, diluted with ethylacetate and treated with 1M HCl solution. Aqueous phase was separated and treated with 1M NaOH solution until pH was 7. Then this aqueous solution was extracted with ethylacetate, concentrated and dried in vacuum and KB-049 was purified by flash chromatography over silica gel (dichloromethane:methanol:triethylamine mixture; 99:0.5:0.5) (E/Z: 4:1) 1H NMR (CDCl3): δ 6.6-6.5 (m, 2H), 6.4 (s, 2H), 6.2 (dd, 2H, J=2 Hz), 3.5 & 3.3 (2 s, 4H), 2.4 (q, 8H, J=7.5 Hz), 2.0 & 1.8 (2 s, 6H), 1.0 (t, 12H, J=7.5 Hz); 13C NMR (CDCl3): δ 157.3, 145.3, 132.3, 127.2, 124.2, 120.2, 119.2, 116.5, 56.7, 48.3, 46.2, 23.2, 21.4, 11.2.

Construction of pSPL3-PKCδ Minigene:

The pSPL3 vector was modified to remove cryptic 5' splice sites as described in a previous publication (25). The pSPL3 vector was digested with BamHI (in the MCS) and NheI. Primers to amplify genomic PKCδ from 3T3L1 cells flanked mouse PKCδ exon 9 and were designed to include the BclI site in the forward primer (in bold type) and BcuI site in the reverse primers (in bold type). The forward primer was designed to amplify 137 bp of 3' intronic sequence such that the product contained the branch point and 3' splice site and the reverse primer included 284 bp 5' intronic sequence and included the 5' splice site II of exon 9. The primers were: forward primer 5' TGGTGATCAAGGAATGAGAC-CTGGGAGACC 3' (SEQ ID NO:6); reverse primer 5' AGAACTAGTTTTCAGTCTACATGACTCCC 3' (SEQ ID NO:7). The product was verified by sequencing and ligated into the digested pSPL3 vector. The overhangs of the selected restriction enzymes can hybridize and this enabled cloning of the PCR product in the proper orientation. The resulting pSPL3-PKCδ minigene was verified by restriction digestion and sequencing.

Statistical Analysis:

The PCR gels were densitometrically analyzed using UN-SCAN-IT™ software (Silk Scientific, Inc.). Western blots were analyzed using AlphaView® software from ProteinSimple™. The mice cohorts (n=5) were obtained and the experiment repeated thrice for reproducibility. PRISM™ software was used for statistical analysis. Two-way ANOVA or matched Student's t-test was used in the analysis. A level of $p<0.05$ was considered statistically significant.

Example 2

Apoptosis in Differentiating 3T3L1 Preadipocytes

The response of preadipocytes and mature adipocytes to serum starvation as an inducer of apoptosis was determined.

Apoptosis was observed in serum-starved preadipocytes (day 0) compared to mature adipocytes (day 10) as seen by DNA fragmentation. FITC Annexin V was used to quantitatively assess cells undergoing apoptosis along with propidium iodide to enable detection of the percentage of cells undergoing either early apoptosis or late apoptosis Annexin V binds to phosphatidylserine which is displayed on the cell membrane of apoptotic cells and PI will stain only dead or damaged cells. The results for Annexin-PI staining indicated apoptosis in serum-starved preadipocytes (day 0) was threefold higher compared to mature adipocytes (day 10). The results also indicated that basal apoptosis was higher in preadipocytes compared to mature adipocytes (FIGS. 1a, b) during 3T3L1 preadipocyte differentiation.

Example 3

Expression of Apoptosis Pathway Genes During Adipogenesis in 3T3L1

Figure 2:
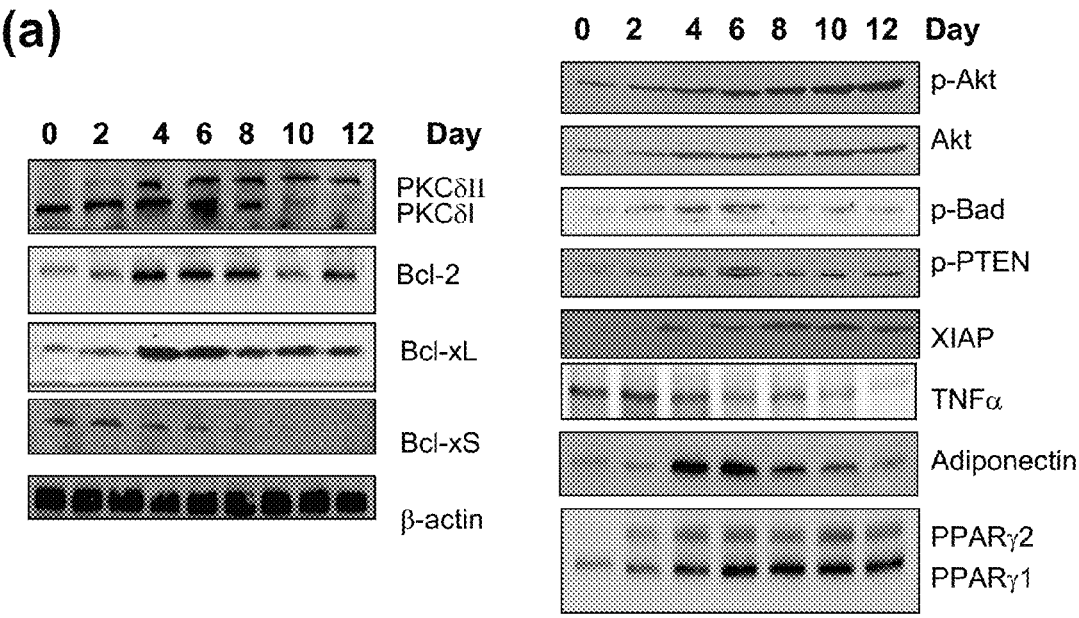
FIG. 2 shows expression of apoptosis genes during 3T3L1 differentiation. (a) Western blot analysis of differentiating 3T3L1 pre-adipocytes from days 0 to 12 using antibodies as indicated in the figure. Between days 4 and 6, a marked shift was observed in the splicing pattern of apoptosis genes. Increase in other survival proteins was also increased between these days. This period marks terminal differentiation of adipocytes. The blots are representative of 4 experiments performed individually with similar results. (b) Graph represents percent PKCδ exon inclusion calculated as PKCδII/(PKCδII+PKCδI)×100 and is representative of ±SEM in four independent experiments.
Figure 2:
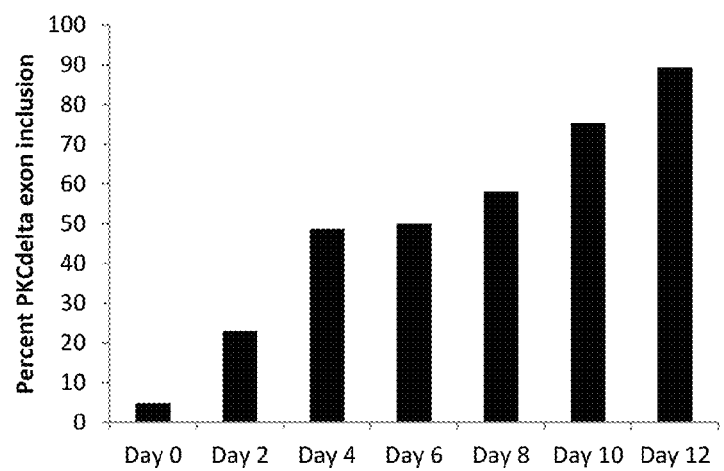

An analysis of gene expression involved in apoptosis during the differentiation of 3T3-L1 pre-adipocytes from days 0 to 12 was performed as they commit and differentiate into mature adipocytes. The data indicated that between days 4 and 6 of differentiation a marked shift was observed in the expression of genes involved in pro-survival pathways and was further accentuated by increase in the splicing of anti-apoptotic proteins. An increase in the pro-survival proteins: PKCδII, Bcl2, Bcl-xL with a simultaneous decrease of the pro-apoptotic proteins: PKCδI and Bcl-xS could be seen. Further, an increase in the phosphorylation of AKT, BAD and PTEN which are necessary for survival pathways was also observed (FIG. 2). Adiponectin and PPARγ are markers of adipogenesis which appear by days 2 to 4 and their levels are maintained during differentiation to mature adipocytes. TNFα is secreted by preadipocytes and its expression decreases as the cells differentiate into mature adipocytes. This data demonstrates a crucial switch in the splicing of apoptosis genes during 3T3L1 adipocyte differentiation. This shift to pro-survival genes renders mature adipocytes resistant to apoptosis.

Example 4

Decreased PKCδII Levels Inhibit Bcl2 and Bcl-xL

Figure 3:
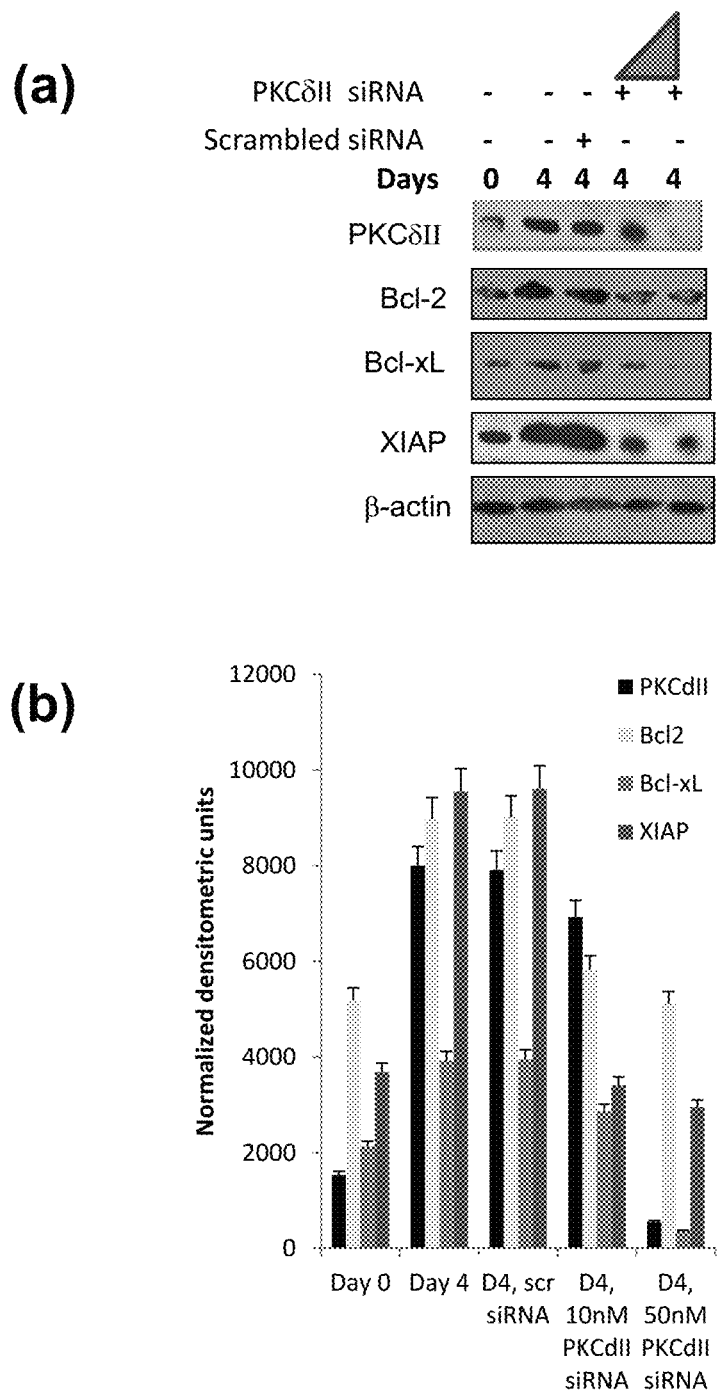
FIG. 3 shows the effect of PKCδII knockdown: 3T3 preadipocytes were transiently transfected on day 0 with either scrambled siRNA, 10 nM or 50 nM PKCδII-specific siRNA. Cells were differentiated as described and whole cell lysates were collected on day 4. (a) Western blot analysis was performed with antibodies as indicated in the figure. The triangle indicates increasing amount (10 or 50 nM) siRNA. The blots are representative of 4 experiments performed individually with similar results. (b) Graph represents densitometric units normalized to β-actin for each protein and is representative of ±SEM in four experiments.

Previous studies in neuronal cells indicated that PKCδII levels directly correlated with expression of Bcl2 and Bcl-xL which are known mediators of survival pathways in cells (19). Accordingly, the question was posed as to whether decreased expression of PKCδII could affect the levels of Bcl2 and Bcl-xL during adipogenesis. 3T3L1 cells were transiently transfected on day 0 with either 10 nM or 50 nM PKCδII-specific siRNA (Ambion, custom designed, specificity and target confirmed in previous studies (19)) along with its scrambled control (to eliminate off-target events) and whole cell lysates collected on day 4. Bcl2 and Bcl-xL levels were evaluated by western blot analysis. A decrease in Bcl2 and Bcl-xL expression was observed along with a decrease in XIAP expression in lysates with PKCδII knockdown (FIG. 3). Bcl2 and XIAP levels decreased by 50% indicating that additional pathways other than PKCδ may be affecting its expression during adipogenesis. However, complete inhibition of BclxL expression was observed in lysates with PKCδII knockdown.

Example 5

Effect of PKCδ Splice Variant Over Expression on Bcl2-Family Survival Genes

Figure 4:
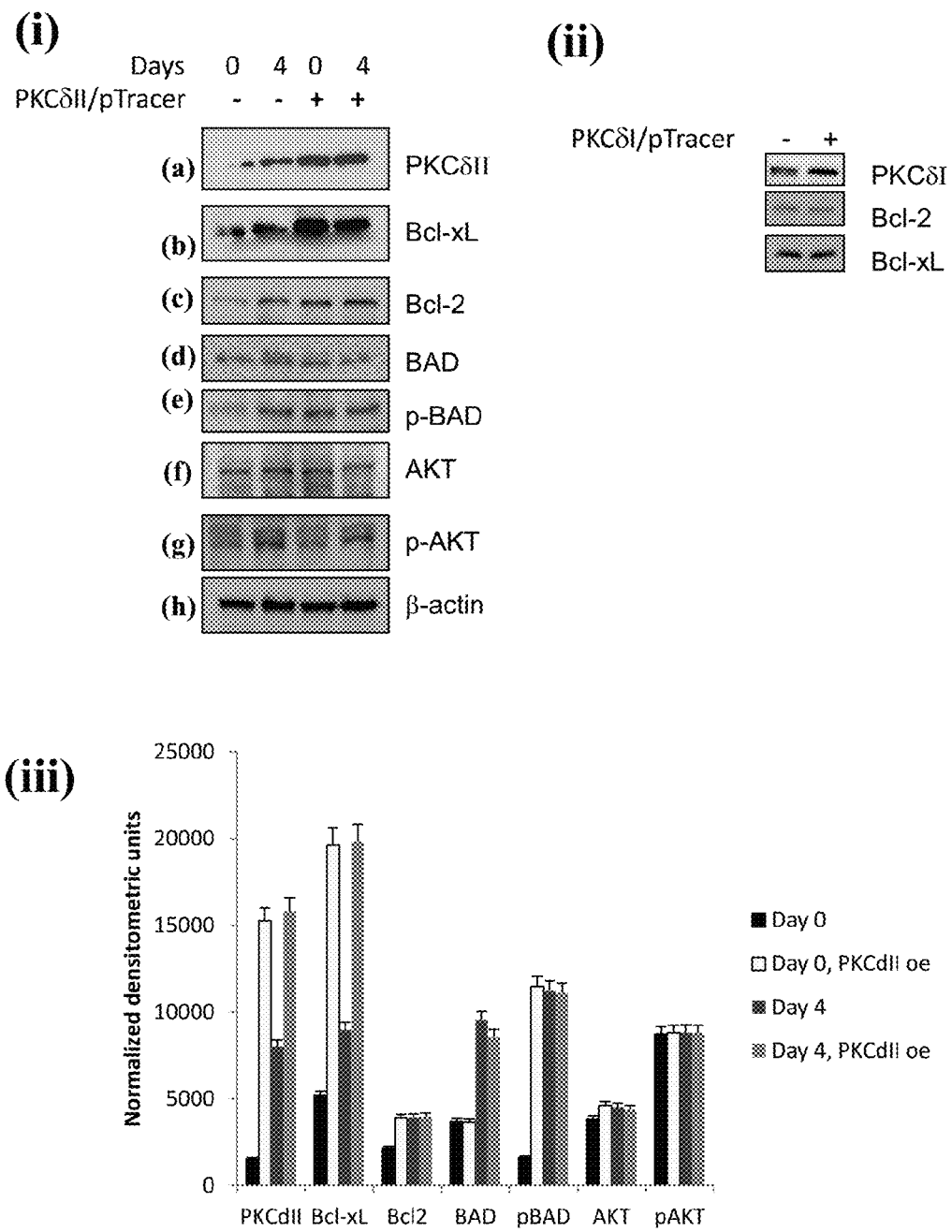
FIG. 4 demonstrates that PKCδII activates a survival pathway: 3T3 preadipocytes were transiently transfected on day −2 with (i) PKCδII-pTracer plasmid or (ii) PKCδI plasmid. Cells were differentiated as described and whole cell lysates were collected on days 0 (for PKCδI and -δII over-expression) and 4 (for PKCδII over-expression). Western blot analysis was performed with antibodies as indicated in the figure. The blots are representative of three experiments performed individually with similar results. (iii) Graph represents densitometric units normalized to β-actin for each protein in control days 0 and 4 and PKCδII over-expression on days 0 and 4 and is representative of ±SEM in three experiments.

The next question posed was whether PKCδII over-expression could affect the expression of the pro-survival proteins Bcl2 and Bcl-xL in 3T3L1 cells. PKCδII-pTracer plasmid (22) was transiently transfected (using 3T3L1 nucleofector kit, Lonza) and western blot analysis was performed on whole cell lysates collected on days 0, 4 and 8. Over-expression of PKCδII increased Bcl2 and Bcl-xL expression (FIG. 4(i) panels a, b, c).

Example 6

PKCδII Expression Activated the Signaling Cascades that Affect Survival Pathways When BAD is in a complex with Bcl2, the mitochondrial mediated survival pathway is inhibited. Upon phosphorylation, p-BAD dissociates thereby allowing Bcl2-Bcl-xL complex to promote survival. The data provided herein (FIG. 1) indicate that phosphorylation of BAD increased on days 4 and 6. To determine whether PKCδII could phosphorylate BAD, PKCδII was transiently transfected on day minus (−) 2 and whole cell lysates collected on days 0 and 4. Phosphorylation of BAD was analyzed by western blot analysis. The results show increased BAD phosphorylation (S136) with PKCδII over expression; total BAD remained constant. Other studies have shown that p-AKT phosphorylates BAD in several other cell types (26, 27). To determine if PKCδII also phosphorylated AKT to further increase p-BAD, phosphorylation of AKT was simultaneously determined. The results indicated that overexpression of PKCδII did not increase AKT phosphorylation (FIG. 4(i) panels d, e, f, g). Hence, PKCδII phosphorylated BAD independent of AKT in 3T3 cells. In separate wells, PKCδI was transiently transfected and levels of Bcl2 and Bcl-xL were measured. Since PKCδI levels are higher in preadipocytes, transient transfection did not increase the levels above 25% of control. Further, PKCδII expression was not observed on day 0. These results indicate that Bcl2 and Bcl-xL levels remained unaffected with PKCδI over-expression (FIG. 4 (ii)).

Example 7

PKCδII and BAD Associate During Adipocyte Differentiation

Since the results indicated an increase in phosphorylation of BAD with PKCδII over-expression, the association pattern of PKCδII and BAD during differentiation of 3T3L1 preadipocytes was investigated. 3T3L1 preadipocytes were collected on days 0 (preadipocytes), 4 (terminal differentiation) and 8 (mature adipocytes) of differentiation and immunoprecipitated with BAD. The blots were then immunoblotted with PKCδII, pBAD and Bcl2. The results (Figure Si) indicate that PKCδII and BAD association peaked by day 4 of differentiation and then declined. Bcl2 associated with BAD on day 0 but then dissociated.

Figure 5:
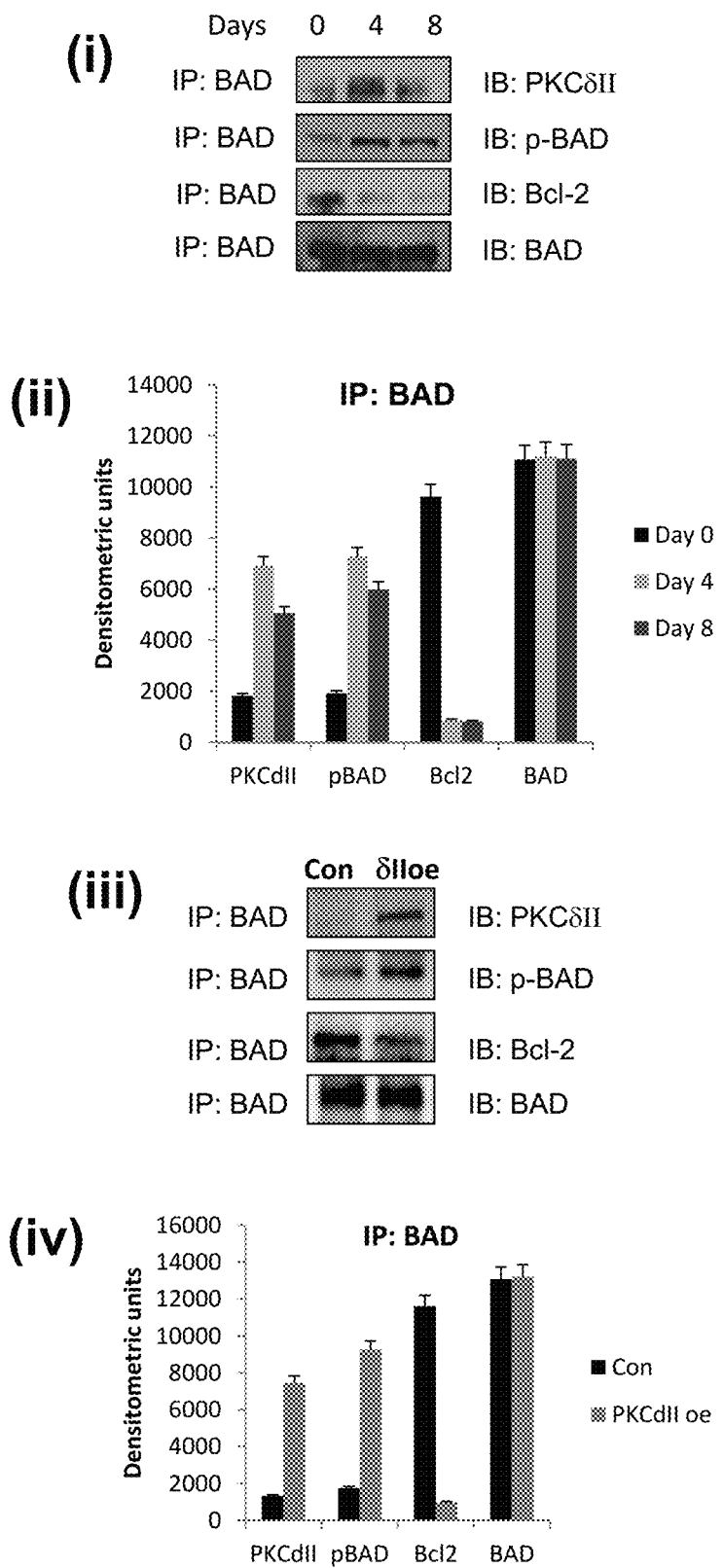
FIG. 5 shows that PKCδII increases BAD phosphorylation. 3T3 preadipocytes were differentiated in vitro and whole cell lysates were collected on days 0, 4 and 8. (i) Cells were immunoprecipitated with BAD antibody and immunoblotted with antibodies as indicated in the figure. Western blot analysis was performed with antibodies as indicated in the figure. The blots are representative of three experiments performed individually with similar results. (ii) Graph represents mean densitometric units from three experiments for each protein and is representative of ±SEM in three experiments.) (iii) 3T3 preadipocytes were transiently transfected on day −2 with PKCδII-pTracer plasmid and whole cell lysates were collected on day 0. Cells were immunoprecipitated with BAD antibody and immunoblotted with antibodies indicated in the figure. Western blot analysis was performed with antibodies as indicated in the figure. The blots are representative of three experiments performed individually with similar results. (iv) Graph represents mean densitometric units from three experiments for each protein and is representative of ±SEM in three experiments.

In separate experiments, PKCδII was over-expressed and cells were immunoprecipitated using BAD antibody. The results (FIG. 5ii) indicate that phosphorylation of BAD increased in PKCδII over-expressing cells compared to control.

Example 8

Effect of PKCδII Expression on Apoptosis

Figure 6:
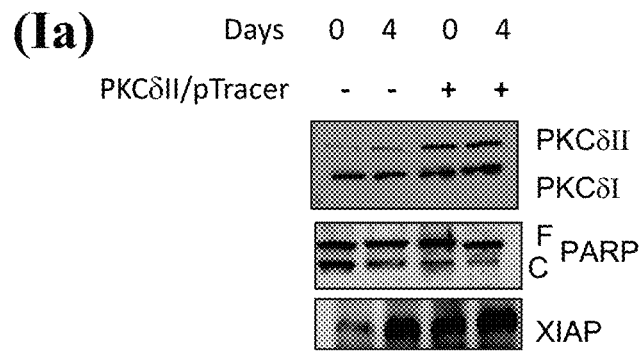
FIG. 6 shows the effect of PKCδII on apoptosis (6I) and adipogenesis (6II): 3T3 preadipocytes were transiently transfected on day −2 with PKCδII-pTracer plasmid. Cells were differentiated as described. (Ia) Whole cell lysates were collected on days 0 and 4. Western blot analysis was performed with antibodies as indicated in the figure. F_PARP: Full-length PARP; C_PARP: Cleaved PARP. The blots are representative of three experiments performed individually with similar results. (Ib) Total apoptosis was measured in day 2 control cells and cells transfected on day −2 with either PKCδI or PKCδII plasmid and collected on day 2 Annexin V-PI was analyzed by flow cytometry and the graph represents five experiments performed separately. (Ic) The graph shows cell viability of either PKCδI or PKCδII as percentage of control cells. Experiments were repeated five times. The measurements were made in triplicate in three separate experiments. Statistical analysis performed by two-way ANOVA; p>0.75 ns, not significant within group; * p<0.0001 highly significant between control and PKCδI or PKCδII expressing cells. Effect of PKCδII on adipogenesis (IIa) Western blot analysis was performed with antibodies as indicated in the figure. The blots are representative of three experiments performed individually with similar results. (IIb) The graph represents three experiments. Statistical analysis performed by two-way ANOVA; p>0.75 ns, not significant within group;  p<0.001 significant, *** p<0.0001 highly significant between control and PKCδII expressing cells on days 0 and 4.
Figure 6:
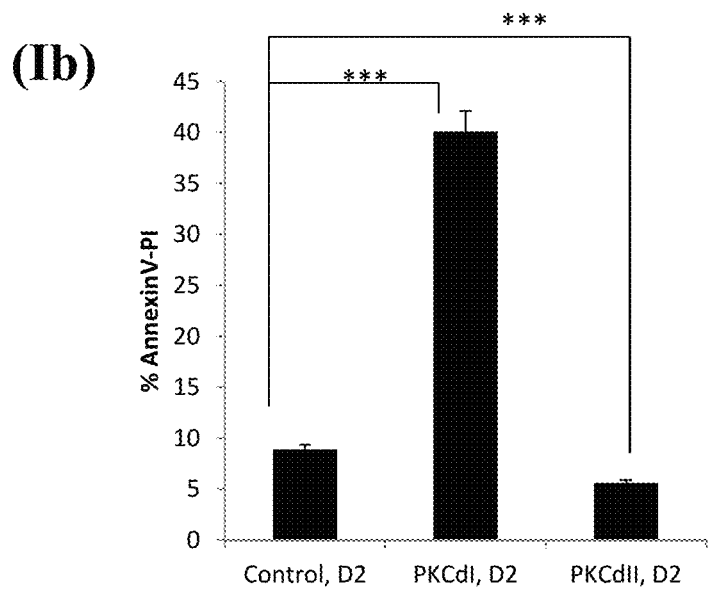
Figure 6:
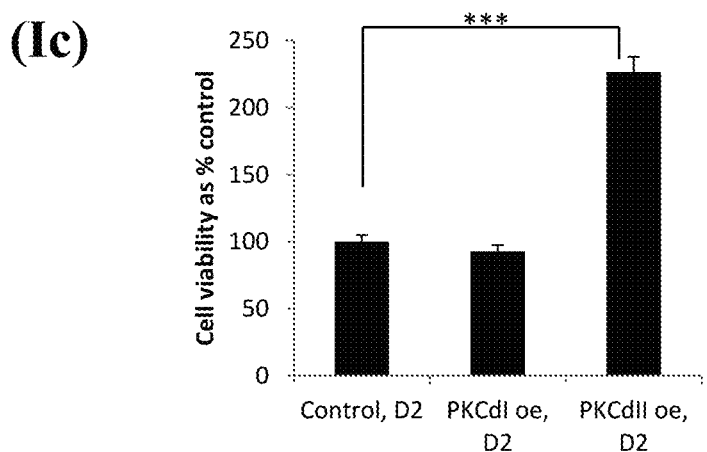
Figure 6:
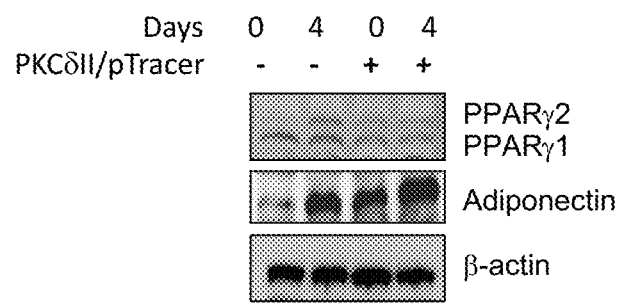
Figure 6:
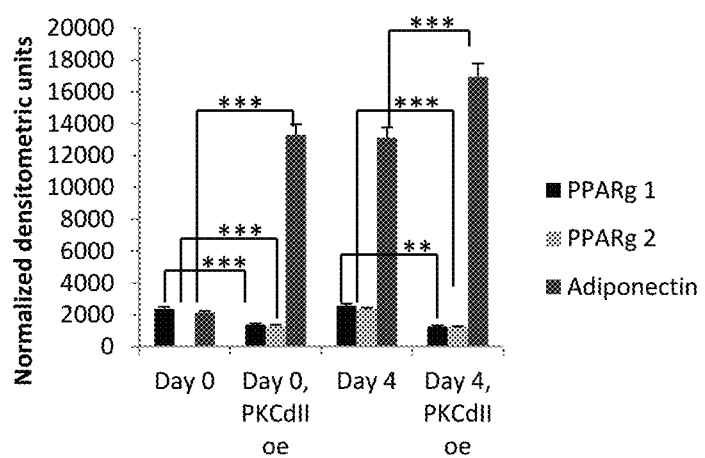

PKCδII is a pro-survival kinase but its role for mediating apoptosis during adipogenesis is not known. Hence, the extent of apoptosis in 3T3L1 preadipocytes in context to PKCδII levels was investigated. 3T3L1 preadipocytes were transiently transfected with PKCδII-pTracer plasmid. The extent of apoptosis was then determined by measuring Poly (ADP-Ribose) polymerase (PARP) cleavage and XIAP expression by western blot analysis (FIG. 6Ia). PARP cleavage which indicates ongoing apoptosis was decreased in cells with PKCδII over-expression while expression of XIAP was increased. Next, apoptosis was measured by annexin V and propidium iodide (PI) staining and cell proliferation was measured with WST1. Increased cell viability was observed in cells over-expressing PKCδII compared to control. PKCδI over-expressing cells showed increased apoptosis (FIG. 6Ib, c). Hence, the results demonstrate that apoptosis levels decrease with increased PKCδII levels.

Example 9

Effect of PKCδII Expression on Adipogenesis

PKCδII expression increased on day 4 when the cells terminally differentiate during adipogenesis. To observe the effect of PKCδII over-expression on adipogenesis, we immunoblotted for adiponectin and PPARγ in 3T3L1 cells over-expressing PKCδII. 3T3L1 preadipocytes were transiently transfected with PKCδII-pTracer plasmid on day −2 and whole cell lysates were collected on days 0 and 4. The results indicate sharply increased expression of adiponectin on days 0 and 4 in cells overexpressing PKCδII compared to control cells. PPARγ1 was expressed on day 0 and by day 4, both PPARγ1 and 2 were expressed in control cells. In cells with PKCδII over-expression, PPARγ 1 and 2 expression on day 0 itself was observed. However, the expression levels of PPARγ 1 and 2 were lower compared to control cells. These results (FIG. 6IIa, b) indicate a dysregulated adipogenesis program when PKCδII is over-expressed.

Example 10

Resveratrol Inhibits PKCδII Levels in 3T3L1 Adipocytes

Figure 7:
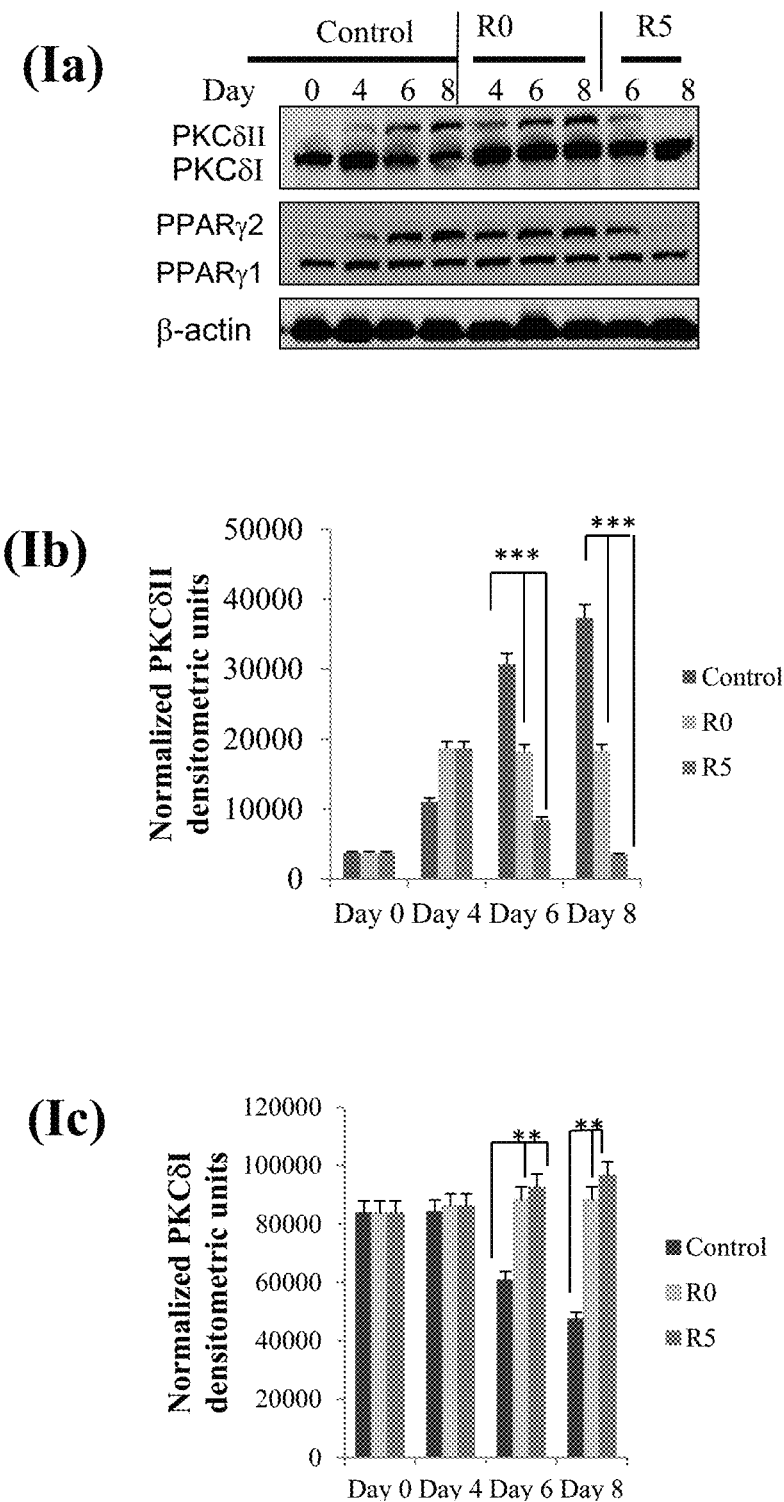
FIG. 7 shows the effect of resveratrol on PKCδ: (I) 3T3 preadipocytes were treated with 25 μM resveratrol on day 0 (R0) or day 5 (R5). Cells were differentiated as described and whole cell lysates were collected on days 0, 4, 6 and 8. (Ia) Western blot analysis was performed with antibodies as indicated in the figure. The blots are representative of three experiments performed individually with similar results. The graphs represent (Ib) PKCδI or (Ic) PKCδII expression normalized to β-actin and represent three experiments performed separately. Statistical analysis performed by two-tail Student's t-test; * p<0.0001 extremely significant between control and day 6, 8 resveratrol treated for PKCδII.  p<0.001 highly significant between control and days 6, 8 resveratrol treated for PKCδI. Effect of resveratrol on apoptosis (II) 3T3 preadipocytes were treated with 2504 resveratrol on day 2 and collected on day 8. (IIa) Oil Red 0 staining for lipid accumulation. (IIb) The graph shows total apoptosis as percent Annexin V-PI staining by flow cytometry. Experiments were repeated 5 times. Statistical analysis performed by two-tail Student's t-test; * p<0.0001 highly significant between day 8 control and day 8 resveratrol. Effect of resveratrol on PKCδ in vivo: (III) C57BL mice were fed a diet with 400 mg resveratrol (RSV) or without resveratrol (control). Adipose tissue was harvested and total RNA was isolated. (IIIa) PCR analysis was performed with primers that detect PKCδI and PKCδII simultaneously and primers for β-actin. The experiments were repeated thrice with similar results. Graphs represent densitometric analysis of (IIIb) PKCδII levels normalized to β-actin and (Inc) PKCδI levels normalized to β-actin. Statistical analysis performed by two-way ANOVA; p>0.75 ns, not significant within group; * p<0.0001 highly significant between control and resveratrol samples.
Figure 7:
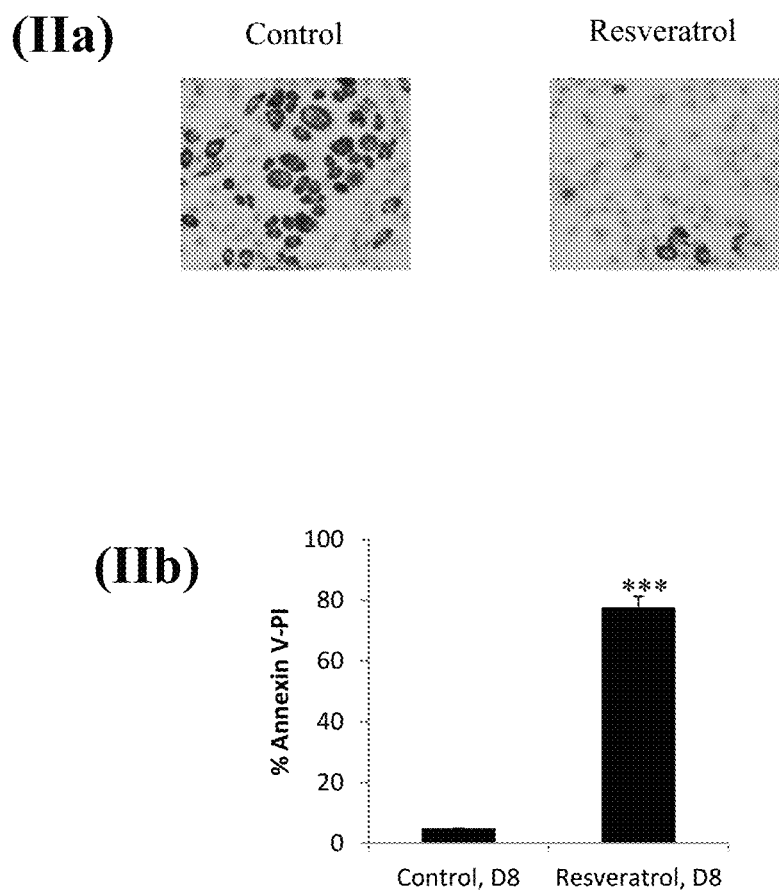
Figure 7:
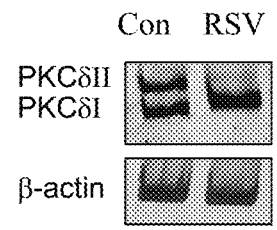
Figure 7:
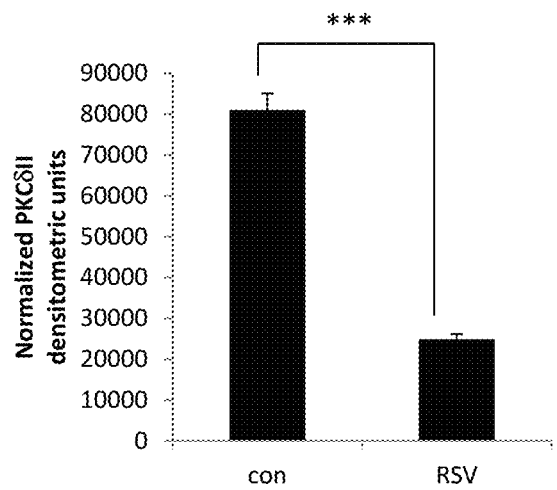
Figure 7:
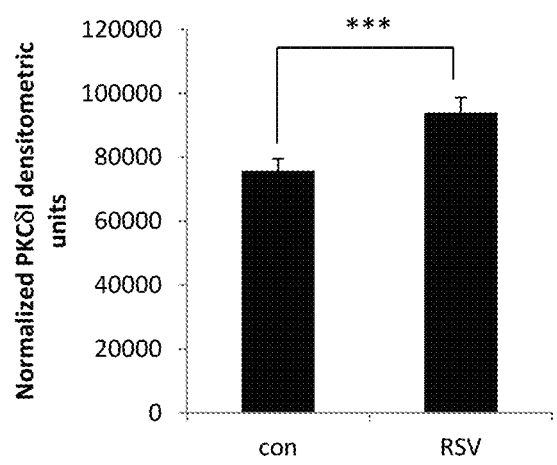

Resveratrol (3,5,4'-trihydroxystilbene) is a naturally occurring polyphenol exhibiting anti-adipogenic activities and also shown to induce apoptosis in adipocytes (28). Several studies have shown its role in inhibiting adipose cell proliferation, lipid accumulation and stimulation of apoptosis and lipolysis in mature adipocytes. Further, resveratrol is shown to modulate alternative splicing of genes (29). However, its mechanisms of action and target proteins in apoptotic pathways during adipogenesis was not determined. Since results provided herein indicated that PKCδII expression modulated apoptosis in 3T3L1 cells, differentiating 3T3L1 preadipocytes were treated with increasing doses of resveratrol (10 to 100 μM). The results indicated that 100 μM resveratrol was detrimental to the cells and our data further indicated 25 μM as the optimal dose (data not shown). Hence, differentiating 3T3L1 cells were treated with 25 μM resveratrol either at day 0 (preadipocyte) or day 5 (mature adipocyte) and whole cell lysates were collected from days 0 to 8. The results showed 25 μM resveratrol administered on day 0 showed less than 10% decrease in PKCδII expression. Resveratrol treatment administered on day 5 (mature adipcoyte) inhibited PKCδII expression levels by 65% on day 6 and by more than 90% on day 8 (FIG. 7I a, b, c). Simultaneously, up to a 50% increase in PKCδI levels was observed on days 6 and 8.

Example 11

Resveratrol Increases Apoptosis and Affects Adipogenesis

Since the results indicated that resveratrol inhibited PKCδII, the effect of reservatrol on adipogenesis and apotosis was determined. PPARγ, a marker of adipogenesis by western blot analysis in differentiating 3T3L1 adipocytes treated with or without 25 μM resveratrol, was measured. The results showed inhibition of PPARγ2 levels on day 8; PPARγ1 levels declined by 30% (FIG. 7Ia). Differentiating 3T3L1 adipocytes were treated with or without 25 μM resveratrol on day 4 and lipid accumulation was determined by Oil Red 0 staining on day 8. The results indicated greater than 75% decline in lipid accumulation in resveratrol treated cells compared to control (FIG. 7IIa). Next, to evaluate the effect of resveratrol on apoptosis, total apoptosis was measured in adipocytes treated with or without 25 μM resveratrol on day 2 and collected on day 8. Measurement of annexin V-PI staining indicated 70% adipocytes were undergoing apoptosis when treated with 25 μM resveratrol (FIG. 7IIb).

Example 12

Resveratrol Inhibits PKCδII Expression In Vivo

To test the effects of resveratrol on PKCδII expression in vivo, RNA derived from adipose tissue from mice fed with 400 mg resveratrol per kg body weight, once daily, was obtained. Earlier studies with these mice had demonstrated that 400 mg resveratrol decreased TNFα levels and increased SIRT1 levels in adipose tissue (23). PCR analysis was performed using primers that detect PKCδI and PKCδII simultaneously for control and resveratrol treated samples. The results (FIG. 7IIIa, b, c) demonstrated a 70% decrease in PKCδII expression and a 25% increase in PKCδI expression in adipose tissue in mice treated with resveratrol.

Example 13

SEAM is a PKCδII-Specific Inhibitor

Currently, there are no inhibitors available for PKCδII. Data indicated that resveratrol inhibited differentiation of 3T3L1 adipocytes and also inhibited PKCδII expression. Hence, structural analogs of resveratrol were evaluated for their ability to inhibit PKCδII expression without disrupting expression of other genes during adipogenesis. Resveratrol is a naturally occurring stilbenoid and hence synthetic stilbenoids were evaluated for their effect on PKCδ splice variants.

Figure 8:
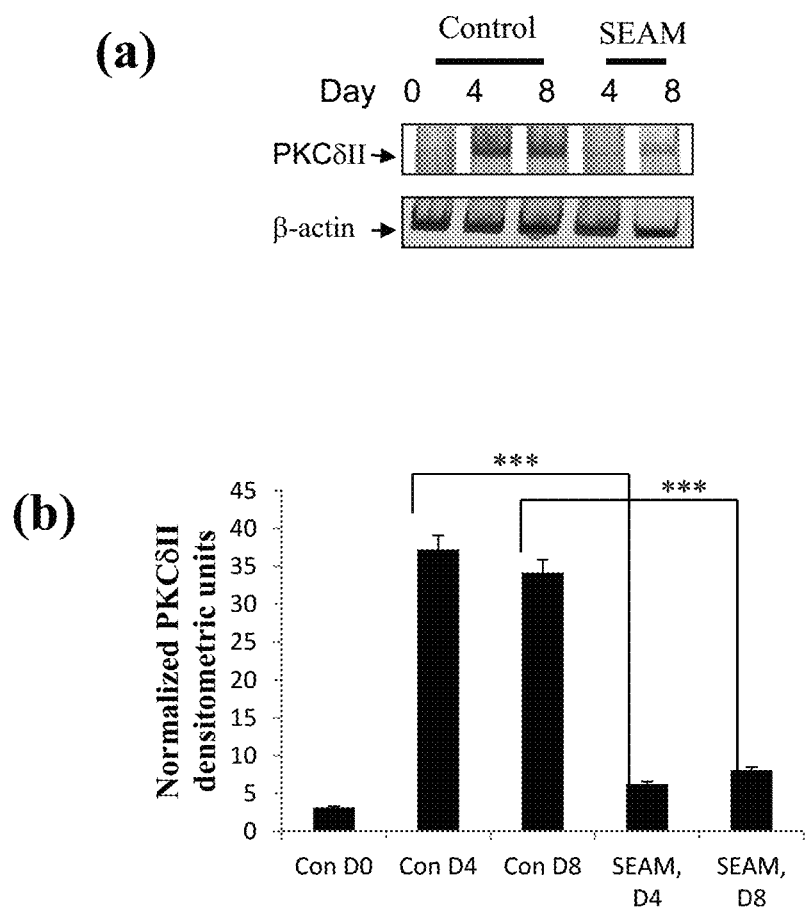
FIG. 8 shows the effect of SEAM on preadipocytes: 3T3L1 preadipocytes were treated with 200 nM resveratrol-SEAM(ana-49) on day 0 and maintained throughout in culture. Cells were differentiated as described and total RNA was collected on days 0 (D0), 4 (D4) and 8 (D8). (a) PCR analysis was performed with PKCδII-specific primers and primers for β-actin. The blots are representative of four experiments performed individually with similar results. (b) Graph represents PKCδII mRNA normalized to β-actin and represents four experiments performed separately. Statistical analysis performed by two-way ANOVA; p>0.75 ns, not significant within group; * p<0.0001 highly significant between control and SEAM on days 4 and 8. (c) and (d) Western blot analysis was performed with antibodies as indicated in the figure. (e) Graph shows apoptosis represented as percent Annexin V-PI positive staining using flow cytometry. (f) Graph shows cell viability as percentage of control cells. Experiments were repeated five times. The measurements were made in triplicate in three separate experiments. Statistical analysis performed by two-tail Student's t-test; * p<0.0001 highly significant between control and SEAM on day 2.
Figure 8:
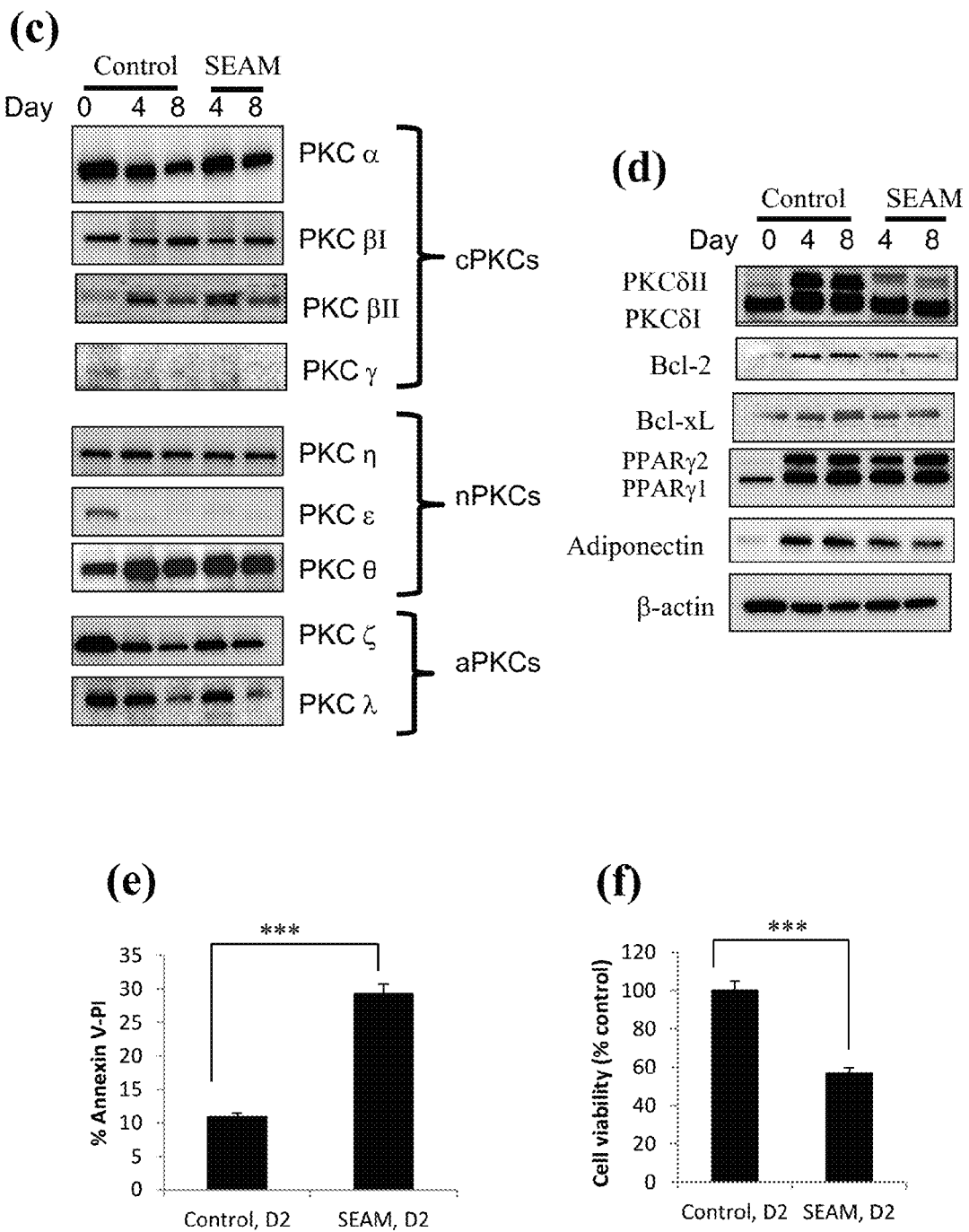
Figure 9:
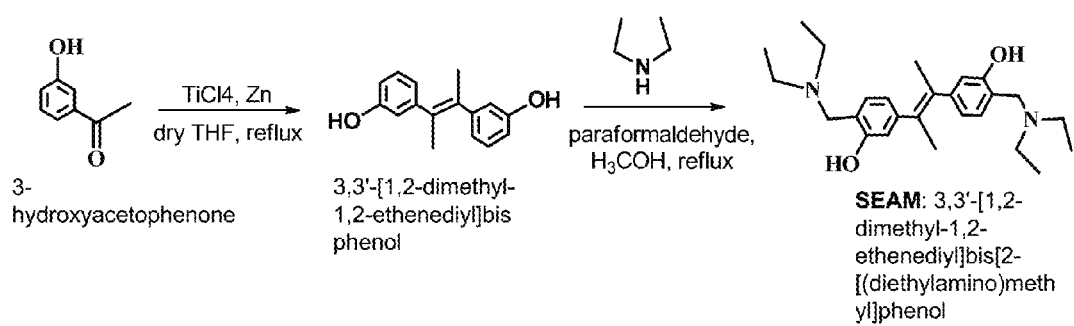
FIG. 9 shows a chemical synthesis outline for SEAM.

3-hydroxystilbene was modified by Mannich coupling to add bis-diethylaminomethyl group (described in Example 1). Several synthetic stilbenoids with structural modifications to the basic resveratrol structure were evaluated. Amongst the tested analogs, SEAM (at 100 nM, See FIG. 9) inhibited PKCδII splicing by 60% while PKCδI expression was not affected (data not shown). A higher dose of 200 nM was then evaluated and the data indicated that SEAM decreased PKCδII by 80% compared to control cells (FIG. 8a). To determine its specificity, immunoblotting for other PKC family isoforms including cPKCs: α, βI, βII, γ; nPKCs: η, ε, θ; aPKCs: ζ, λ was performed. SEAM did not affect the expression levels of these PKC isoforms (FIG. 8b). Interestingly, treatment with SEAM did not affect PKCδI levels; however, Bcl2 levels decreased by 40% while BclxL levels decreased by 20% (FIG. 8c).

Immunoblotting for PPARγ and adiponectin was also performed to determine whether SEAM affected differentiation of 3T3L1 cells. SEAM treatment decreased PPARγ2 by 5% and adiponectin by 20% on days 4 and 8 compared to control. Total apoptosis was measured by flow cytometry using Annexin V-PI staining (FIG. 8d). To determine whether SEAM was toxic to cells, cell viability was evaluated upon treatment of 200 nM SEAM in 3T3L1 cells. Cytotoxicity was measured using the 3-(4, 5-Dimethyl-2-thiazolyl)-2, 5-diphenyl-2H-tetrazolium bromide (MTT) assay. This assay measures the reducing potential of the cell using a colorimetric reaction. Viable cells reduce the MTS reagent to a colored formazan product. Data indicated that 3T3L1 cells treated with SEAM were viable with their apoptosis levels increased compared to control cells (FIG. 8e). This data is in concurrence with the extent of apoptosis seen with decreased PKCδII levels in 3T3L1 cells.

Example 14

Effect of SEAM on PKCδ Splicing Minigene

Figure 10:
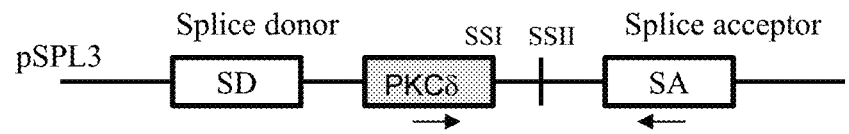
FIG. 10 (a-c) shows the effects of SEAM on the PKCδ splicing minigene: 3T3 preadipocytes were transiently transfected on day 0 with pSPL3-PKCδ splicing minigene. Cells were treated with SEAM. Cells were differentiated as described and total RNA collected on day 4. PCR was performed using SD to SA primers on the minigene. Graph represents percent 5' splice site (SS) utilization of PKCδ exon 9 calculated as SSII/(SSII+SSI)×100 and is representative of ±SEM in four independent experiments.
Figure 10:
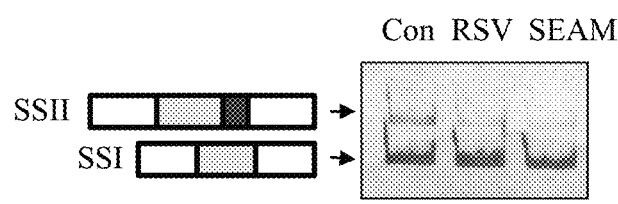
Figure 10:
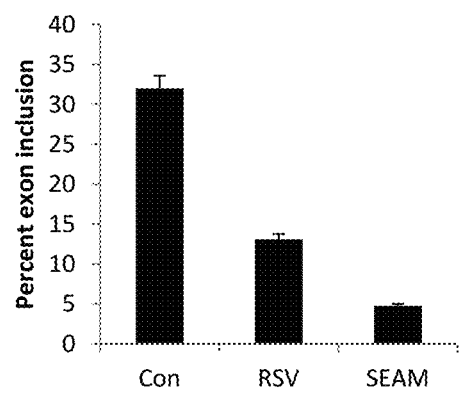

Splicing minigenes are advantageous to study alternative splicing events without influence from endogenous factors. Hence to determine whether resveratrol affected PKCδ alternative splicing directly and was not due to effects of resveratrol on 3T3L1 differentiation, PKCδ splicing minigene was used. pSPL3-PKCδ (as described in Example 1) was transiently transfected on day 0. Utilization of 5' splice site I on exon 9 gave rise to PKCδI while utilization of downstream 5' splice site II gave rise to PKCδII. After 24 hours, the cells were treated with 200 nM SEAM. Cells were harvested on day 2 and total RNA isolated for RT-PCR using primers for SD and SA on pSPL3-PKCδ. The results indicate that SEAM inhibited utilization of 5' splice site II. See FIG. 10.

We claim:

1. A method for specifically inhibiting expression of PKCδII, PKCδVIII, or any homolog thereof in a subject in need thereof, the method comprising administration of a therapeutically effective amount of a compound of Formula II or a salt, prodrug or metabolite thereof

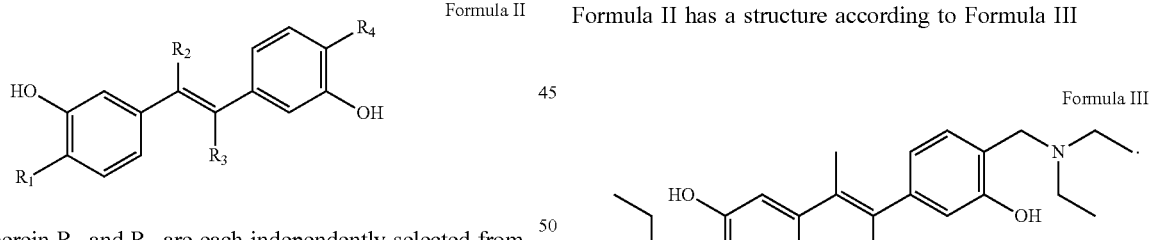

Formula II wherein $R_1$ and $R_4$ are each independently selected from the group consisting of —$N(R_7)_2$ and —$R_8N(R_7)_2$;

wherein $R_2$ and $R_3$ are each independently selected from the group consisting of hydrogen, and substituted and unsubstituted alkyl, heteroalkyl, aryl, aralkyl, alkenyl, and alkynyl groups having from 1 to 30 carbon atoms;

wherein each occurrence of $R_7$ is independently selected from the group consisting of substituted and unsubstituted alkyl and heteroalkyl groups having from 1 to 30 carbon atoms; and wherein $R_8$ is selected from the group consisting of substituted and unsubstituted alkyl and heteroalkyl groups having from 1 to 12 carbon atoms, wherein the effective amount is effective to specifically inhibit expression of PKCδII, PKCδVIII, or any homolog thereof in the subject.

2. The method of claim 1, wherein the compound of Formula II comprises an amino or amino-alkyl substituent.

3. The method of claim 2, wherein the substituent is a dialkyl-amino or a dialkyl-amino-alkyl substituent.

4. The method of claim 1, wherein the compound of Formula II is administered in a pharmaceutical formulation comprising compound of Formula II and a pharmaceutically acceptable carrier.

5. The method of claim 1, wherein the compound of Formula II has a structure according to Formula III Formula III 6. The method of claim 1, wherein the subject demonstrates decreased levels of PKCδII, PKCδVIII, or any homolog thereof after administration as compared to levels prior to the administration.

7. The method of claim 1, wherein the subject demonstrates increased weight loss and/or fat loss after administration as compared to prior to the administration.

8. The method of claim 6, wherein the expression of PKCδI or any homolog thereof in the subject is not effected.

9. The method of claim 1, wherein the subject has a decreased number of adipocytes after administration as compared to prior to the administration.

10. The method of claim 1, wherein the effective amount is effective without affecting expression of PKCδI or any homolog thereof in the subject.

\* \* \* \* \*

SEQUENCE LISTING

<160> NUMBER OF SEQ ID NOS: 7

<210> SEQ ID NO 1
<211> LENGTH: 24
<212> TYPE: DNA
<213> ORGANISM: Artificial Sequence
<220> FEATURE:
<223> OTHER INFORMATION: PKC delta forward primer

<400> SEQUENCE: 1
gtggccaacc tgtgtggtat caac                                      24

<210> SEQ ID NO 2
<211> LENGTH: 23
<212> TYPE: DNA
<213> ORGANISM: Artificial Sequence
<220> FEATURE:
<223> OTHER INFORMATION: PKC delta reverse primer

<400> SEQUENCE: 2
ctctgccagc agcaccttgc caa                                       23

<210> SEQ ID NO 3
<211> LENGTH: 27
<212> TYPE: DNA
<213> ORGANISM: Artificial Sequence
<220> FEATURE:
<223> OTHER INFORMATION: PKC delta II-specific antisense primer

<400> SEQUENCE: 3
tcgcaggtct cactactgtc cttttcc                                   27

<210> SEQ ID NO 4
<211> LENGTH: 21
<212> TYPE: DNA
<213> ORGANISM: Artificial Sequence
<220> FEATURE:
<223> OTHER INFORMATION: beta-actin forward primer

<400> SEQUENCE: 4
cttcattgac ctcaactcat g                                         21

```
<210> SEQ ID NO 5
<211> LENGTH: 22
<212> TYPE: DNA
<213> ORGANISM: Artificial Sequence
<220> FEATURE:
<223> OTHER INFORMATION: beta-actin reverse primer

<400> SEQUENCE: 5
tgtcatggat gaccttggcc ag                                              22

<210> SEQ ID NO 6
<211> LENGTH: 30
<212> TYPE: DNA
<213> ORGANISM: Artificial Sequence
<220> FEATURE:
<223> OTHER INFORMATION: forward primer for exon 9 of PKC delta

<400> SEQUENCE: 6
tggtgatcaa ggaatgagac ctgggagacc                                      30

<210> SEQ ID NO 7
<211> LENGTH: 29
<212> TYPE: DNA
<213> ORGANISM: Artificial Sequence
<220> FEATURE:
<223> OTHER INFORMATION: reverse primer for exon 9 of PKC delta

<400> SEQUENCE: 7
agaactagtt ttcagtctac atgactccc                                       29
```